(12) United States Patent
Taub et al.

(10) Patent No.: US 9,541,556 B2
(45) Date of Patent: *Jan. 10, 2017

(54) METHOD AND APPARATUS FOR PROVIDING GLYCEMIC CONTROL

(71) Applicant: Abbott Diabetes Care Inc., Alameda, CA (US)

(72) Inventors: Marc Barry Taub, Mountain View, CA (US); Timothy Christian Dunn, San Francisco, CA (US); Nathan Christopher Crouther, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 415 days.

This patent is subject to a terminal disclaimer.

(21) Appl. No.: 14/089,322

(22) Filed: Nov. 25, 2013

(65) Prior Publication Data

US 2014/0081104 A1  Mar. 20, 2014

Related U.S. Application Data

(63) Continuation of application No. 12/476,093, filed on Jun. 1, 2009, now Pat. No. 8,591,410.

(Continued)

(51) Int. Cl.
*A61B 5/00* (2006.01)
*G01N 33/66* (2006.01)
(Continued)

(52) U.S. Cl.
CPC ............. *G01N 33/66* (2013.01); *A61B 5/1118* (2013.01); *A61B 5/14532* (2013.01);
(Continued)

(58) Field of Classification Search
CPC .......... G01N 33/66; G06F 19/30; G06F 19/34; G06F 19/345; G06F 19/3487; A61B 5/1118; A61B 5/14532; A61B 5/14546; A61B 5/14865; A61B 5/6849; A61B 5/7246
(Continued)

(56) References Cited

U.S. PATENT DOCUMENTS 3,581,062 A  5/1971  Aston
3,926,760 A  12/1975  Allen et al.
(Continued)

FOREIGN PATENT DOCUMENTS

DE  4401400  7/1995
EP  0098592  1/1984
(Continued)

OTHER PUBLICATIONS

Armour, J. C., et al., "Application of Chronic Intravascular Blood Glucose Sensor in Dogs", *Diabetes*, vol. 39, 1990, pp. 1519-1526.
(Continued)

*Primary Examiner* — William Thomson
*Assistant Examiner* — John R Downey
(74) *Attorney, Agent, or Firm* — Jackson & Co., LLP

(57) ABSTRACT

Methods to provide glycemic control and therapy management based on monitored glucose data, and current and/or target Hb1AC levels are provided. Systems to provide glycemic control and therapy management based on monitored glucose data, and current and/or target Hb1AC levels are provided. Kits to provide glycemic control and therapy management based on monitored glucose data, and current and/or target Hb1AC levels are provided.

20 Claims, 15 Drawing Sheets

Related U.S. Application Data

(60) Provisional application No. 61/097,504, filed on Sep. 16, 2008, provisional application No. 61/057,786, filed on May 30, 2008.

(51) Int. Cl.
  *A61B 5/145* (2006.01)
  *A61B 5/1486* (2006.01)
  *G06F 19/00* (2011.01)
  *A61B 5/11* (2006.01)

(52) U.S. Cl.
  CPC ...... *A61B 5/14546* (2013.01); *A61B 5/14865* (2013.01); *A61B 5/6849* (2013.01); *A61B 5/7246* (2013.01); *G06F 19/3481* (2013.01); *A61B 5/7275* (2013.01)

(58) Field of Classification Search
  USPC .................................................. 600/300, 301
  See application file for complete search history.

(56) References Cited

U.S. PATENT DOCUMENTS

| | | |
|---|---|---|
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,425,920 A | 1/1984 | Bourland et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,715 A | 6/1994 | Berg |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,394,877 A | 3/1995 | Orr et al. |
| 5,402,780 A | 4/1995 | Faasse, Jr. |
| 5,408,999 A | 4/1995 | Singh et al. |
| 5,410,326 A | 4/1995 | Goldstein |
| 5,411,647 A | 5/1995 | Johnson et al. |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,543,326 A | 8/1996 | Heller et al. |
| 5,552,997 A | 9/1996 | Massart |
| 5,555,190 A | 9/1996 | Derby et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Nigel et al. |
| 5,640,954 A | 6/1997 | Pfeiffer et al. |
| 5,653,239 A | 8/1997 | Pompei et al. |
| 5,665,222 A | 9/1997 | Heller et al. |
| 5,711,001 A | 1/1998 | Bussan et al. |
| 5,711,861 A | 1/1998 | Ward et al. |
| 5,726,646 A | 3/1998 | Bane et al. |
| 5,735,285 A | 4/1998 | Albert et al. |
| 5,748,103 A | 5/1998 | Flach et al. |
| 5,772,586 A | 6/1998 | Heinonen et al. |
| 5,791,344 A | 8/1998 | Schulman et al. |
| 5,807,375 A | 9/1998 | Gross et al. |
| 5,820,551 A | 10/1998 | Hill et al. |
| 5,822,715 A | 10/1998 | Worthington et al. |
| 5,875,186 A | 2/1999 | Belanger et al. |
| 5,899,855 A | 5/1999 | Brown |
| 5,914,026 A | 6/1999 | Blubaugh, Jr. et al. |
| 5,919,141 A | 7/1999 | Money et al. |
| 5,925,021 A | 7/1999 | Castellano et al. |
| 5,942,979 A | 8/1999 | Luppino |
| 5,951,521 A | 9/1999 | Mastrototaro et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,987,353 A | 11/1999 | Khatchatrian et al. |
| 5,995,860 A | 11/1999 | Sun et al. |
| 6,001,067 A | 12/1999 | Shults et al. |
| 6,004,278 A | 12/1999 | Botich et al. |
| 6,022,315 A | 2/2000 | Iliff |

(56) References Cited

U.S. PATENT DOCUMENTS

| | | |
|---|---|---|
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,071,391 A | 6/2000 | Gotoh et al. |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,096,364 A | 8/2000 | Bok et al. |
| 6,103,033 A | 8/2000 | Say et al. |
| 6,115,622 A | 9/2000 | Minoz |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,823 A | 10/2000 | Hughes et al. |
| 6,134,461 A | 10/2000 | Say et al. |
| 6,141,573 A | 10/2000 | Kurnik et al. |
| 6,143,164 A | 11/2000 | Heller et al. |
| 6,144,837 A | 11/2000 | Quy |
| 6,157,850 A | 12/2000 | Diab et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,405,066 B1 | 6/2002 | Essenpreis et al. |
| 6,413,393 B1 | 7/2002 | Van Antwerp et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,045 B1 | 11/2002 | Holker et al. |
| 6,484,046 B1 | 11/2002 | Say et al. |
| 6,493,069 B1 | 12/2002 | Nagashimada et al. |
| 6,498,043 B1 | 12/2002 | Schulman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,546,268 B1 | 4/2003 | Ishikawa et al. |
| 6,551,494 B1 | 4/2003 | Heller et al. |
| 6,554,798 B1 | 4/2003 | Mann et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,631,281 B1 | 10/2003 | Kastle |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,730,025 B1 | 5/2004 | Platt |
| 6,730,200 B1 | 5/2004 | Stewart et al. |
| 6,733,446 B2 | 5/2004 | Lebel et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,789,195 B1 | 9/2004 | Prihoda et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,837,858 B2 | 1/2005 | Cunningham et al. |
| 6,850,790 B2 | 2/2005 | Berner et al. |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman IV et al. |

(56) References Cited

U.S. PATENT DOCUMENTS

| | | |
|---|---|---|
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,015,817 B2 | 3/2006 | Copley et al. |
| 7,016,713 B2 | 3/2006 | Gardner et al. |
| 7,022,219 B2 | 4/2006 | Mansouri et al. |
| 7,024,245 B2 | 4/2006 | Lebel et al. |
| 7,025,774 B2 | 4/2006 | Freeman et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,046,153 B2 | 5/2006 | Oja et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,171,274 B2 | 1/2007 | Starkweather et al. |
| 7,179,226 B2 | 2/2007 | Crothall et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,299,082 B2 | 11/2007 | Feldman et al. |
| 7,310,544 B2 | 12/2007 | Brister et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,424,318 B2 | 9/2008 | Brister et al. |
| 7,429,258 B2 | 9/2008 | Angel et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,501,053 B2 | 3/2009 | Karinka et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,697,967 B2 | 4/2010 | Stafford |
| 7,699,775 B2 | 4/2010 | Desai et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,310 B2 | 6/2010 | Taub |
| 7,736,344 B2 | 6/2010 | Moberg et al. |
| 7,754,093 B2 | 7/2010 | Forrow et al. |
| 7,763,042 B2 | 7/2010 | Iio et al. |
| 7,766,829 B2 | 8/2010 | Sloan et al. |
| 7,768,387 B2 | 8/2010 | Fennell |
| 7,771,352 B2 | 8/2010 | Shults et al. |
| 7,778,680 B2 | 8/2010 | Goode et al. |
| 7,811,231 B2 | 10/2010 | Jin et al. |
| 7,813,809 B2 | 10/2010 | Strother et al. |
| 7,822,454 B1 | 10/2010 | Alden et al. |
| 7,826,382 B2 | 11/2010 | Sicurello et al. |
| 7,866,026 B1 | 1/2011 | Wang et al. |
| 7,873,595 B2 | 1/2011 | Singh et al. |
| 7,889,069 B2 | 2/2011 | Fifolt et al. |
| 7,899,511 B2 | 3/2011 | Shults et al. |
| 7,899,545 B2 | 3/2011 | John |
| 7,914,460 B2 | 3/2011 | Melker et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,972,296 B2 | 7/2011 | Braig et al. |
| 7,976,466 B2 | 7/2011 | Ward et al. |
| 7,978,063 B2 | 7/2011 | Baldus et al. |
| 7,996,158 B2 | 8/2011 | Hayter et al. |
| 8,005,524 B2 | 8/2011 | Brauker et al. |
| 8,010,174 B2 | 8/2011 | Goode et al. |
| 8,010,256 B2 | 8/2011 | Oowada |
| 8,116,837 B2 | 2/2012 | Huang |
| 8,160,900 B2 | 4/2012 | Taub et al. |
| 8,192,394 B2 | 6/2012 | Estes et al. |
| 8,216,138 B1 | 7/2012 | McGarraugh et al. |
| 8,255,026 B1 | 8/2012 | Al-Ali |
| 8,282,549 B2 | 10/2012 | Brauker et al. |
| 8,374,668 B1 | 2/2013 | Hayter et al. |
| 8,457,703 B2 | 6/2013 | Al-Ali |
| 8,461,985 B2 | 6/2013 | Fennell et al. |
| 8,583,205 B2 | 11/2013 | Budiman et al. |
| 8,597,570 B2 | 12/2013 | Terashima et al. |
| 8,600,681 B2 | 12/2013 | Hayter et al. |
| 8,710,993 B2 | 4/2014 | Hayter et al. |
| 8,834,366 B2 | 9/2014 | Hayter et al. |
| 8,845,536 B2 | 9/2014 | Brauker et al. |
| 2001/0020124 A1 | 9/2001 | Tamada |
| 2001/0037060 A1 | 11/2001 | Thompson et al. |
| 2001/0037366 A1 | 11/2001 | Webb et al. |
| 2001/0047604 A1 | 12/2001 | Valiulis |
| 2002/0019022 A1 | 2/2002 | Dunn et al. |
| 2002/0042090 A1 | 4/2002 | Heller et al. |
| 2002/0054320 A1 | 5/2002 | Ogino |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0111832 A1 | 8/2002 | Judge |
| 2002/0117639 A1 | 8/2002 | Paolini et al. |
| 2002/0120186 A1 | 8/2002 | Keimel |
| 2002/0128594 A1 | 9/2002 | Das et al. |
| 2002/0133107 A1 | 9/2002 | Darcey |

(56) References Cited

U.S. PATENT DOCUMENTS

| | | |
|---|---|---|
| 2002/0147135 A1 | 10/2002 | Schnell |
| 2002/0161288 A1 | 10/2002 | Shin et al. |
| 2002/0188748 A1 | 12/2002 | Blackwell et al. |
| 2003/0005464 A1 | 1/2003 | Gropper et al. |
| 2003/0021729 A1 | 1/2003 | Moller et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0114897 A1 | 6/2003 | Von Arx et al. |
| 2003/0134347 A1 | 7/2003 | Heller et al. |
| 2003/0147515 A1 | 8/2003 | Kai et al. |
| 2003/0163351 A1 | 8/2003 | Brown |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212379 A1 | 11/2003 | Bylund et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0015102 A1 | 1/2004 | Cummings et al. |
| 2004/0024553 A1 | 2/2004 | Monfre et al. |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0063435 A1 | 4/2004 | Sakamoto et al. |
| 2004/0064068 A1 | 4/2004 | DeNuzzio et al. |
| 2004/0073266 A1 | 4/2004 | Haefner et al. |
| 2004/0078215 A1 | 4/2004 | Dahlin et al. |
| 2004/0093167 A1 | 5/2004 | Braig et al. |
| 2004/0099529 A1 | 5/2004 | Mao et al. |
| 2004/0106858 A1 | 6/2004 | Say et al. |
| 2004/0111017 A1 | 6/2004 | Say et al. |
| 2004/0117204 A1 | 6/2004 | Mazar et al. |
| 2004/0122353 A1 | 6/2004 | Shahmirian et al. |
| 2004/0128225 A1 | 7/2004 | Thompson et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138588 A1 | 7/2004 | Saikley et al. |
| 2004/0147872 A1 | 7/2004 | Thompson |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193090 A1 | 9/2004 | Lebel et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0223985 A1 | 11/2004 | Dunfiled et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027181 A1 | 2/2005 | Goode et al. |
| 2005/0031689 A1 | 2/2005 | Shults et al. |
| 2005/0038680 A1 | 2/2005 | McMahon |
| 2005/0043598 A1 | 2/2005 | Goode, Jr. et al. |
| 2005/0049179 A1 | 3/2005 | Davidson et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096516 A1 | 5/2005 | Soykan et al. |
| 2005/0112169 A1 | 5/2005 | Brauker et al. |
| 2005/0113648 A1 | 5/2005 | Yang et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0134731 A1 | 6/2005 | Lee et al. |
| 2005/0137530 A1 | 6/2005 | Campbell et al. |
| 2005/0143635 A1 | 6/2005 | Kamath et al. |
| 2005/0154271 A1 | 7/2005 | Rasdal et al. |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0184153 A1 | 8/2005 | Auchinleck |
| 2005/0187442 A1 | 8/2005 | Cho et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0251033 A1 | 11/2005 | Scarantino et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |

(56) References Cited

U.S. PATENT DOCUMENTS

| | | |
|---|---|---|
| 2006/0091006 A1 | 5/2006 | Wang et al. |
| 2006/0142651 A1 | 6/2006 | Brister et al. |
| 2006/0154642 A1 | 7/2006 | Scannell |
| 2006/0166629 A1 | 7/2006 | Reggiardo |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0189863 A1 | 8/2006 | Peyser et al. |
| 2006/0193375 A1 | 8/2006 | Lee et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2006/0290496 A1 | 12/2006 | Peeters et al. |
| 2006/0293607 A1 | 12/2006 | Alt et al. |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027383 A1 | 2/2007 | Peyser et al. |
| 2007/0027507 A1 | 2/2007 | Burdett et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0056858 A1 | 3/2007 | Chen et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0068807 A1 | 3/2007 | Feldman et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078818 A1 | 4/2007 | Zvitz et al. |
| 2007/0093786 A1 | 4/2007 | Goldsmith et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0149875 A1 | 6/2007 | Ouyang et al. |
| 2007/0163880 A1 | 7/2007 | Woo et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0176867 A1 | 8/2007 | Reggiardo et al. |
| 2007/0179434 A1 | 8/2007 | Weinert et al. |
| 2007/0191701 A1 | 8/2007 | Feldman et al. |
| 2007/0191702 A1 | 8/2007 | Yodfat et al. |
| 2007/0199818 A1 | 8/2007 | Petyt et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0227911 A1 | 10/2007 | Wang et al. |
| 2007/0228071 A1 | 10/2007 | Kamen et al. |
| 2007/0231846 A1 | 10/2007 | Cosentino et al. |
| 2007/0232878 A1 | 10/2007 | Kovatchev et al. |
| 2007/0233013 A1 | 10/2007 | Schoenberg |
| 2007/0235331 A1 | 10/2007 | Simpson et al. |
| 2007/0249922 A1 | 10/2007 | Peyser et al. |
| 2007/0255321 A1 | 11/2007 | Gerber et al. |
| 2007/0255348 A1 | 11/2007 | Holtzclaw |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0004904 A1 | 1/2008 | Tran |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058773 A1 | 3/2008 | John |
| 2008/0060955 A1 | 3/2008 | Goodnow |
| 2008/0061961 A1 | 3/2008 | John |
| 2008/0066305 A1 | 3/2008 | Wang et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0102441 A1 | 5/2008 | Chen et al. |
| 2008/0108942 A1 | 5/2008 | Brister et al. |
| 2008/0114228 A1 | 5/2008 | McCluskey et al. |
| 2008/0119703 A1 | 5/2008 | Brister et al. |
| 2008/0119708 A1 | 5/2008 | Budiman |
| 2008/0125636 A1* | 5/2008 | Ward .................. A61B 5/7475 600/365 |
| 2008/0127052 A1 | 5/2008 | Rostoker |
| 2008/0139910 A1 | 6/2008 | Mastrototaro et al. |
| 2008/0148873 A1 | 6/2008 | Wang |
| 2008/0161666 A1 | 7/2008 | Feldman et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0218180 A1 | 9/2008 | Waffenschmidt et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0262469 A1 | 10/2008 | Brister et al. |
| 2008/0267823 A1 | 10/2008 | Wang et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0314395 A1 | 12/2008 | Kovatchev et al. |
| 2008/0319085 A1 | 12/2008 | Wright et al. |
| 2008/0319294 A1 | 12/2008 | Taub |
| 2008/0319295 A1 | 12/2008 | Bernstein et al. |

(56) References Cited

U.S. PATENT DOCUMENTS

| | | |
|---|---|---|
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0036747 A1 | 2/2009 | Hayter et al. |
| 2009/0036758 A1 | 2/2009 | Brauker et al. |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0062633 A1 | 3/2009 | Brauker et al. |
| 2009/0062635 A1 | 3/2009 | Brauker et al. |
| 2009/0063964 A1 | 3/2009 | Huang et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085873 A1 | 4/2009 | Betts et al. |
| 2009/0088614 A1 | 4/2009 | Taub |
| 2009/0093687 A1 | 4/2009 | Telfort et al. |
| 2009/0099436 A1 | 4/2009 | Brister et al. |
| 2009/0105560 A1 | 4/2009 | Solomon |
| 2009/0105570 A1 | 4/2009 | Sloan et al. |
| 2009/0105571 A1 | 4/2009 | Fennell et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143661 A1 | 6/2009 | Taub et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0253973 A1 | 10/2009 | Bashan et al. |
| 2009/0287073 A1 | 11/2009 | Boock et al. |
| 2009/0287074 A1 | 11/2009 | Shults et al. |
| 2009/0294277 A1 | 12/2009 | Thomas et al. |
| 2009/0296742 A1 | 12/2009 | Sicurello et al. |
| 2009/0298182 A1 | 12/2009 | Schulat et al. |
| 2009/0299151 A1 | 12/2009 | Taub et al. |
| 2009/0299152 A1 | 12/2009 | Taub et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022988 A1 | 1/2010 | Wochner et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081905 A1 | 4/2010 | Bommakanti et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0093786 A1 | 4/2010 | Watanabe et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121167 A1 | 5/2010 | McGarraugh et al. |
| 2010/0121169 A1 | 5/2010 | Petisce et al. |
| 2010/0141656 A1 | 6/2010 | Krieftewirth |
| 2010/0145172 A1 | 6/2010 | Petisce et al. |
| 2010/0152554 A1 | 6/2010 | Steine et al. |
| 2010/0160759 A1 | 6/2010 | Celentano et al. |
| 2010/0160760 A1 | 6/2010 | Shults et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168657 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0174266 A1 | 7/2010 | Estes |

(56) References Cited

U.S. PATENT DOCUMENTS

| | | |
|---|---|---|
| 2010/0179399 A1 | 7/2010 | Goode et al. |
| 2010/0179400 A1 | 7/2010 | Brauker et al. |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179405 A1 | 7/2010 | Goode et al. |
| 2010/0179407 A1 | 7/2010 | Goode et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185073 A1 | 7/2010 | Goode et al. |
| 2010/0185074 A1 | 7/2010 | Goode et al. |
| 2010/0185075 A1 | 7/2010 | Brister et al. |
| 2010/0185175 A1 | 7/2010 | Kamen et al. |
| 2010/0191082 A1 | 7/2010 | Brister et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |
| 2010/0213080 A1 | 8/2010 | Celentano et al. |
| 2010/0230285 A1 | 9/2010 | Hoss et al. |
| 2010/0234710 A1 | 9/2010 | Budiman et al. |
| 2010/0257490 A1 | 10/2010 | Lyon et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0280441 A1 | 11/2010 | Willinska et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0326842 A1 | 12/2010 | Mazza et al. |
| 2011/0004085 A1 | 1/2011 | Mensinger et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0031986 A1 | 2/2011 | Bhat et al. |
| 2011/0054282 A1 | 3/2011 | Nekoomaram et al. |
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0081726 A1 | 4/2011 | Berman et al. |
| 2011/0082484 A1 | 4/2011 | Saravia et al. |
| 2011/0105955 A1 | 5/2011 | Yudovsky et al. |
| 2011/0106126 A1 | 5/2011 | Love et al. |
| 2011/0112696 A1 | 5/2011 | Yodfat et al. |
| 2011/0148905 A1 | 6/2011 | Simmons et al. |
| 2011/0190603 A1 | 8/2011 | Stafford |
| 2011/0191044 A1 | 8/2011 | Stafford |
| 2011/0208027 A1 | 8/2011 | Wagner et al. |
| 2011/0208155 A1 | 8/2011 | Palerm et al. |
| 2011/0213225 A1 | 9/2011 | Bernstein et al. |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0287528 A1 | 11/2011 | Fern et al. |
| 2011/0288574 A1 | 11/2011 | Curry et al. |
| 2011/0289497 A1 | 11/2011 | Kiaie et al. |
| 2011/0320130 A1 | 12/2011 | Valdes et al. |
| 2012/0078071 A1 | 3/2012 | Bohm et al. |
| 2012/0088995 A1 | 4/2012 | Fennell et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0209099 A1 | 8/2012 | Ljuhs et al. |
| 2012/0215462 A1 | 8/2012 | Goode et al. |
| 2013/0035575 A1 | 2/2013 | Mayou et al. |
| 2013/0184547 A1 | 7/2013 | Taub et al. |
| 2013/0235166 A1 | 9/2013 | Jones et al. |
| 2014/0121480 A1 | 5/2014 | Budiman et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/74753 | 12/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2005/041766 | 5/2005 |
| WO | WO-2005/089103 | 9/2005 |
| WO | WO-2005/119524 | 12/2005 |
| WO | WO-2006/024671 | 3/2006 |
| WO | WO-2006/079114 | 7/2006 |
| WO | WO-2006/086423 | 8/2006 |
| WO | WO-2006/118947 | 11/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/001366 | 1/2008 |
| WO | WO-2008/086541 | 7/2008 |
| WO | WO-2010/077329 | 7/2010 |

OTHER PUBLICATIONS

Bennion, N., et al., "Alternate Site Glucose Testing: A Crossover Design", *Diabetes Technology & Therapeutics* vol. 4 No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Mediated Enzyme Electrode for Amperometric Determination of Glucose", *Analytical Chemistry*, vol. 56, No. 4, 1984, 667-671.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

(56) References Cited

OTHER PUBLICATIONS

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jovanovic, L., "The Role of Continuous Glucose Monitoring in Gestational Diabetes Mellitus", *Diabetes Technology & Therapeutics* vol. 2 Sup. 1, 2000, pp. S67-S71.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", IEEE Press, 2004, pp. 141, 142, 548, 549.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Parker, R., et al., "Robust H∞ Glucose Control in Diabetes Using a Physiological Model", *AIChE Journal*, vol. 46, No. 12, 2000, pp. 2537-2549.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Suarez, L., "New ADA Recommendations More Comprehensive", *Diabetic Microvascular Complications Today*, 2005, pp. 10-12.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

PCT Application No. PCT/US2009/045766, International Preliminary Report on Patentability mailed Dec. 9, 2010.

(56) References Cited

OTHER PUBLICATIONS

PCT Application No. PCT/US2009/045766, International Search Report and Written Opinion of the International Searching Authority mailed Jul. 14, 2009.
U.S. Appl. No. 12/476,093, Advisory Action mailed May 23, 2013.
U.S. Appl. No. 12/476,093, Notice of Allowance mailed Oct. 3, 2013.
U.S. Appl. No. 12/476,093, Office Action mailed Jul. 20, 2012.
U.S. Appl. No. 12/476,093, Office Action mailed Jul. 25, 2012.
U.S. Appl. No. 12/476,093, Office Action mailed Jul. 3, 2013.
U.S. Appl. No. 12/476,093, Office Action mailed Mar. 11, 2013.
U.S. Appl. No. 12/476,107, Advisory Action mailed Sep. 23, 2013.
U.S. Appl. No. 12/476,107, Office Action mailed Dec. 26, 2012.
U.S. Appl. No. 12/476,107, Office Action mailed Feb. 7, 2012.
U.S. Appl. No. 12/476,107, Office Action mailed Jul. 16, 2013.
Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1070.
Garg, S., et al., "Improvement in Glycemic Excursions with a Transcutaneous, Real-Time Continuous Glucose Sensor", *Diabetes Care*, vol. 29, No. 1, 2006, pp. 44-50.
Li, Y., et al., "In Vivo Release From a Drug Delivery MEMS Device", *Journal of Controlled Release*, vol. 100, 2004, 99. 211-219.
Panteleon, A. E., et al., "The Role of the Independent Variable to Glucose Sensor Calibration", *Diabetes Technology & Therapeutics*, vol. 5, No. 3, 2003, pp. 401-410.
U.S. Appl. No. 12/476,107, Notice of Allowance mailed Oct. 24, 2014.

\* cited by examiner

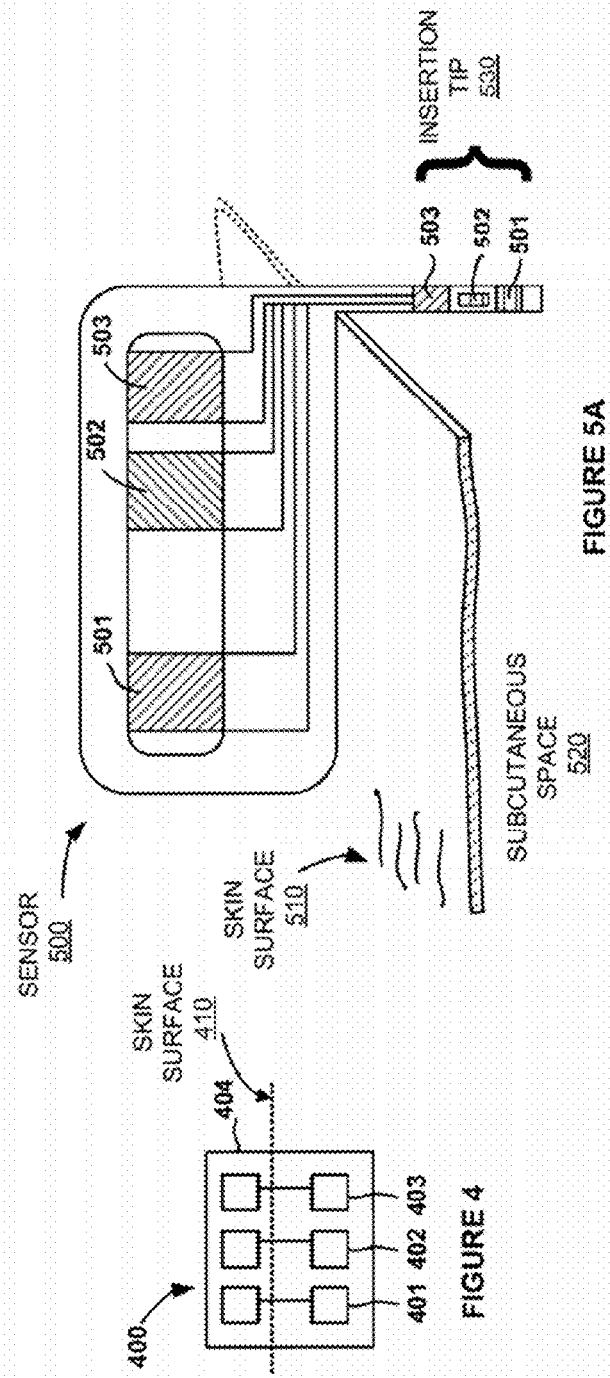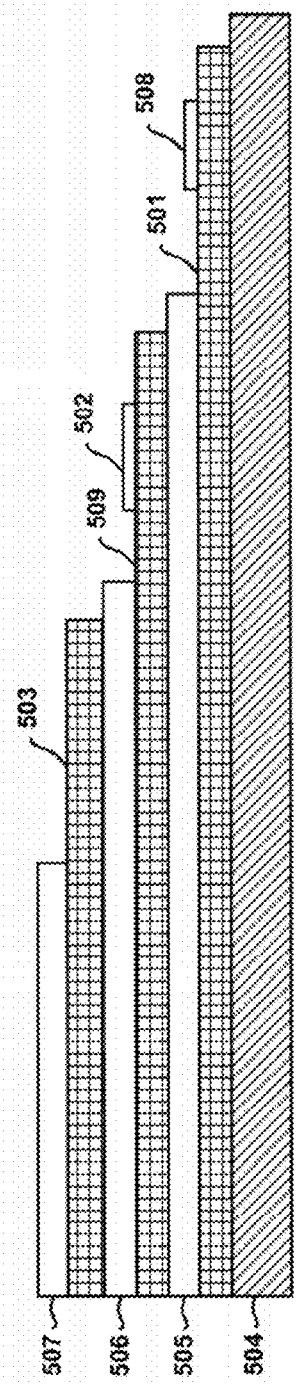

| Demographics | | Frequency / N (%) |
|---|---|---|
| Gender | Female | 50 / 90 (55.6 %) |
| | Male | 40 / 90 (44.4 %) |
| Race | Caucasian | 80 / 90 (88.9 %) |
| | Non-Caucasian | 10 / 90 (11.1 %) |
| Age | 18-34 | 23 / 90 (25.6 %) |
| | 35-54 | 55 / 90 (61.1 %) |
| | 55+ | 12 / 90 (13.3 %) |

| Characteristics | N | Mean ± SD (Min, Max) |
|---|---|---|
| Age (Years) | 90 | 42.4 ± 11.4 (18.4, 71.9) |
| Weight (lbs) | 90 | 168 ± 32.5 (112, 265) |
| Height (Inches) | 90 | 66.9 ± 4.1 (59.0, 79.0) |
| BMI | 90 | 26.4 ± 4.2 (18.2, 41.6) |
| Duration of Diabetes (Years) | 90 | 23.1 ± 10.1 (5.6, 51.4) |
| Daily total insulin dosage (units) | 90 | 42.9 ± 14.9 (17.0, 105) |
| Baseline A1C Level (%) | 89* | 7.1 ± 0.8 (5.4, 9.1) |

FIG. 6

|  | N | Baseline HbA1C <7.0% | Baseline HbA1C ≥ 7.0% | P-value |
|---|---|---|---|---|
| Male | 89 | 47% (16/34) | 44% (24/55) | 0.753 |
| Age* | 89 | 43 ± 11 | 42 ± 11 | 0.481 |
| BMI | 89 | 26 ± 4 | 27 ± 4 | 0.350 |
| Diabetes Duration* | 89 | 24 ± 11 | 22 ± 10 | 0.440 |
| *Years | | | | |

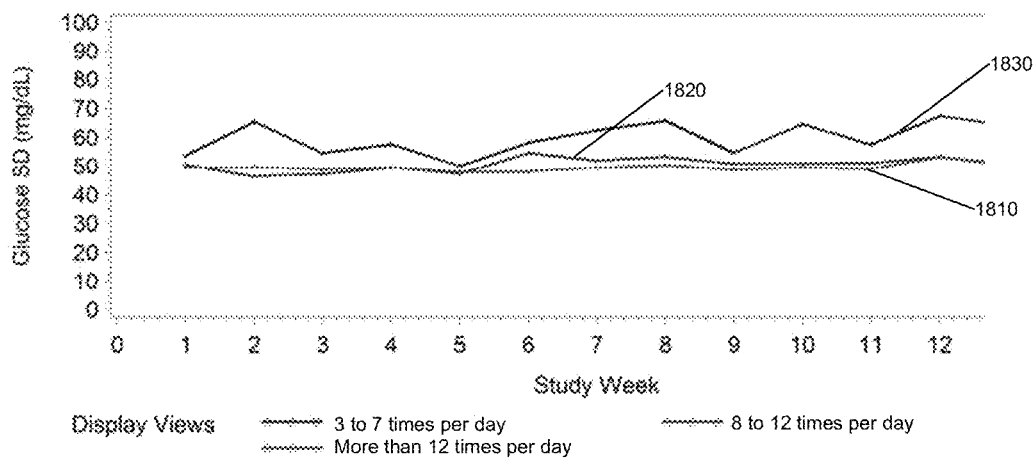

FIG. 18

| Subject ID | Patient 1 | Patient 2 | Patient 3 |
|---|---|---|---|
| Recent HbA1C (%) | 5.8 | 5.6 | 6.1 |
| 30 day avg CGM (mg/dL) | 100 | 110 | 157 |
| 30 day glycability (mg/dL)/% HbA1C | 17.3 | 19.7 | 25.7 |
| 30 day % Hypoglycemia | 29.9 | 12.5 | 3.3 |
| Action for HbA1C: | Decrease target due to HbA1C | No change | Decrease target due to HbA1C |
| Action for hypoglycemia: | Increase target due to hypo rate. | Increase target due to hypo rate. | No change |
| Recommendations: CGM target = Target A1C * glycability | Increase targets: HbA1C = 6.5 CGM avg = 113 | Increase targets: HbA1C = 6.0 CGM avg = 118 | Decrease targets: HbA1C = 5.5 CGM avg = 142 |

FIG. 19

METHOD AND APPARATUS FOR PROVIDING GLYCEMIC CONTROL

RELATED APPLICATIONS

The present application is a continuation of U.S. patent application Ser. No. 12/476,093 filed Jun. 1, 2009, now U.S. Pat. No. 8,591,410, which claims priority under 35 USC §119(e) to U.S. Provisional application No. 61/057,786 filed May 30, 2008, entitled "Method and Apparatus for Providing Glycemic Control" and U.S. Provisional Application No. 61/097,504 filed Sep. 16, 2008, entitled "Therapy Management Based on Continuous Glucose Data and Meal Information", the disclosures of each of which are incorporated herein by reference for all purposes.

BACKGROUND

The detection of the level of analytes, such as glucose, lactate, oxygen, and the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Accordingly, of interest are devices that allow a user to test for one or more analytes, and provide glycemic control and therapy management.

SUMMARY

Embodiments of the present disclosure include method and apparatus for receiving mean glucose value information of a patient based on a predetermined time period, receiving an HbA1C level of the patient, determining a correlation between the received mean glucose value information and the HbA1C level, and determining a target HbA1C level based on the determined correlation.

BRIEF DESCRIPTION OF THE DRAWINGS

FIG. 4 shows a schematic diagram of an embodiment of an analyte sensor according to the present disclosure;

FIGS. 5A-5B show a perspective view and a cross sectional view, respectively of another embodiment an analyte sensor;

FIG. 6 provides a tabular illustration of the demographic and characteristics of participants in the 90 days continuous glucose monitoring system use study in one aspect;

FIG. 18 is a graphical illustration of the glycemic variability measured as the standard deviation on a weekly basis of the subjects between the number of times daily the subjects viewed the real time continuously monitored glucose levels in one aspect;

FIG. 19 is a tabular illustration of three hypothetical subjects to evaluate and modify target continuously monitored glucose levels based on HbA1C measurements, average 30 day CGM data, and percentage of duration in hypoglycemic condition over the 30 day period in one aspect;

DETAILED DESCRIPTION

Figure 1:
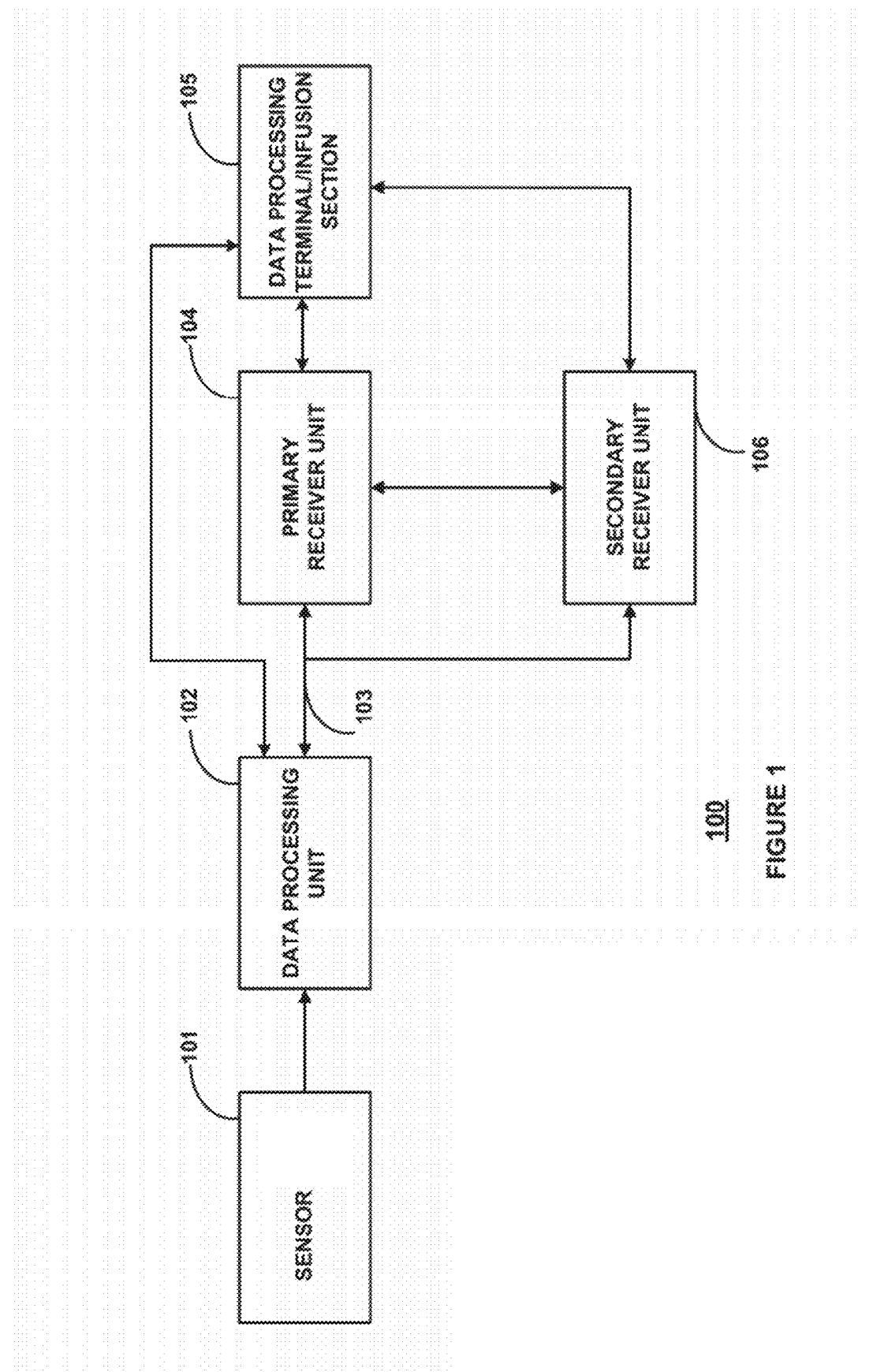
FIG. 1 shows a block diagram of an embodiment of a data monitoring and management system according to the present disclosure.

Before the present disclosure is described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

It must be noted that as used herein and in the appended claims, the singular forms "a", "an", and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and devices for detecting at least one analyte such as glucose in body fluid. Embodiments relate to the continuous and/or automatic in vivo monitoring of the level of one or more analytes using a continuous analyte monitoring system that includes an analyte sensor at least a portion of which is to be positioned beneath a skin surface of a user for a period of time and/or the discrete monitoring of one or more analytes using an in vitro blood glucose ("BG") meter and an analyte test strip. Embodiments include combined or combinable devices, systems and methods and/or transferring data between an in vivo continuous system and a BG meter system.

Embodiments of the present disclosure include method and apparatus for receiving mean glucose value information of a patient based on a predetermined time period, receiving an HbA1C (also referred to as A1C) level of the patient, determining a correlation between the received mean glucose value information and the HbA1C level, and determining a target HbA1C level based on the determined correlation, for example, for diabetes management or physiological therapy management. Additionally, in certain embodiments of the present disclosure there are provided method, apparatus, and system for receiving mean glucose value information of a patient based on a predetermined time period, receiving a current HbA1C level of the patient and a target HbA1C level of the patient, determining a correlation between the received mean glucose value information and the retrieved current and target HbA1C levels, updating the target HbA1C level based on the determined correlation, and determining one or more parameters associated with the physiological condition of the patient based on the updated target HbA1C level.

Accordingly, embodiments include analyte monitoring devices and systems that include an analyte sensor—at least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Embodiments of the analyte sensors of the subject disclosure may be configured for monitoring the level of the analyte over a time period which may range from minutes, hours, days, weeks, or longer.

Of interest are analyte sensors, such as glucose sensors, that are capable of in vivo detection of an analyte for about one hour or more, e.g., about a few hours or more, e.g., about a few days of more, e.g., about three days or more, e.g., about five days or more, e.g., about seven days or more, e.g., about several weeks or at least one month. Future analyte levels may be predicted based on information obtained, e.g., the current analyte level at time $t_0$, the rate of change of the analyte, etc. Predictive alarms may notify the user of predicted analyte levels that may be of concern in advance of the user's analyte level reaching the future level. This provides the user an opportunity to take corrective action.

FIG. 1 shows a data monitoring and management system such as, for example, an analyte (e.g., glucose) monitoring system 100 in accordance with certain embodiments. Embodiments of the subject disclosure are further described primarily with respect to glucose monitoring devices and systems, and methods of glucose detection, for convenience only and such description is in no way intended to limit the scope of the disclosure. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 includes a sensor 101, a data processing unit 102 connectable to the sensor 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104 and/or the data processing terminal 105 and/or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or a bi-directional communication device. A docking cradle may recharge a power supply.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit 102 may include a fixation element such as adhesive or the like to secure it to the user's body. A mount (not shown) attachable to the user and mateable with the data processing unit 102 may be used. For example, a mount may include an adhesive surface. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In certain embodiments, the primary receiver unit 104 may include an analog interface section including an RF receiver and an antenna that is configured to communicate with the data processing unit 102 via the communication link 103, and a data processing section for processing the received data from the data processing unit 102 such as data decoding, error detection and correction, data clock generation, data bit recovery, etc., or any combination thereof.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone, Blackberry device, a Palm device or similar phone), mp3 player, pager, GPS (global positioning system) device and the like), or a drug delivery device, each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include an infusion device such as an insulin infusion pump or the like, which may be configured to administer insulin to patients, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In certain embodiments, the data processing terminal 105, which may include an insulin pump, may be configured to receive the analyte signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1, may use one or more of: an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements), while avoiding potential data collision and interference.

Figure 2:
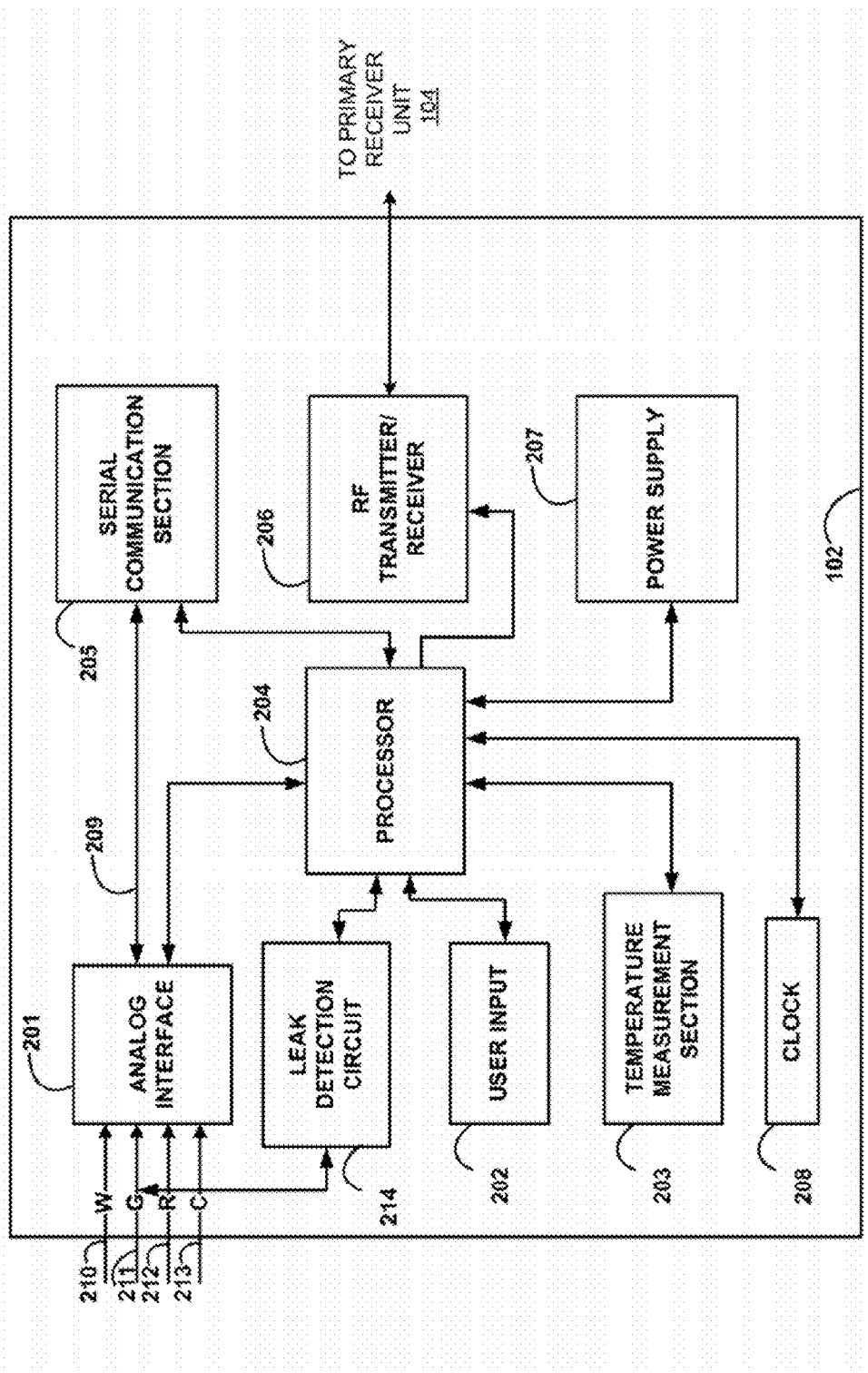
FIG. 2 shows a block diagram of an embodiment of the transmitter unit of the data monitoring and management system of FIG. 1.

FIG. 2 shows a block diagram of an embodiment of a data processing unit of the data monitoring and detection system shown in FIG. 1. The data processing unit 102 thus may include one or more of an analog interface 201 configured to communicate with the sensor 101 (FIG. 1), a user input 202, and a temperature measurement section 203, each of which is operatively coupled to a processor 204 such as a central processing unit (CPU). User input and/or interface components may be included or a data processing unit may be free of user input and/or interface components. In certain embodiments, one or more application-specific integrated circuits (ASIC) may be used to implement one or more functions or routines associated with the operations of the data processing unit (and/or receiver unit) using for example one or more state machines and buffers.

Further shown in FIG. 2 are a serial communication section 205 and an RF transmitter 206, each of which is also operatively coupled to the processor 204. The RF transmitter 206, in some embodiments, may be configured as an RF receiver or an RF transmitter/receiver, such as a transceiver, to transmit and/or receive data signals. Moreover, a power supply 207, such as a battery, may also be provided in the data processing unit 102 to provide the necessary power for the data processing unit 102. Additionally, as can be seen from the Figure, clock 208 may be provided to, among others, supply real time information to the processor 204.

As can be seen in the embodiment of FIG. 2, the sensor 101 (FIG. 1) includes four contacts, three of which are electrodes—work electrode (W) 210, reference electrode (R) 212, and counter electrode (C) 213, each operatively coupled to the analog interface 201 of the data processing unit 102. This embodiment also shows optional guard contact (G) 211. Fewer or greater electrodes may be employed. For example, the counter and reference electrode functions may be served by a single counter/reference electrode, there may be more than one working electrode and/or reference electrode and/or counter electrode, etc.

In certain embodiments, a unidirectional input path is established from the sensor 101 (FIG. 1) and/or manufacturing and testing equipment to the analog interface 201 of the data processing unit 102, while a unidirectional output is established from the output of the RF transmitter 206 of the data processing unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in certain embodiments, via the data path described above, the data processing unit 102 is configured to transmit to the primary receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the data processing unit 102 for operation upon completion of the manufacturing process as well as for direct communication for diagnostic and testing purposes.

The processor 204 may be configured to transmit control signals to the various sections of the data processing unit 102 during the operation of the data processing unit 102. In certain embodiments, the processor 204 also includes memory (not shown) for storing data such as the identification information for the data processing unit 102, as well as the data signals received from the sensor 101. The stored information may be retrieved and processed for transmission to the primary receiver unit 104 under the control of the processor 204. Furthermore, the power supply 207 may include a commercially available battery.

The data processing unit 102 is also configured such that the power supply section 207 is capable of providing power to the data processing unit 102 for a minimum period of time, e.g., at least about one month, e.g., at least about three months or more, of continuous operation. The minimum may be after (i.e., in addition to), a period of time, e.g., up to about eighteen months, of being stored in a low- or no-power (non-operating) mode. In certain embodiments, this may be achieved by the processor 204 operating in low power modes in the non-operating state, for example, drawing no more than minimal current, e.g., approximately 1 µA of current or less. In certain embodiments, a manufacturing process of the data processing unit 102 may place the data processing unit 102 in the lower power, non-operating state (i.e., post-manufacture sleep mode). In this manner, the shelf life of the data processing unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present disclosure, the power supply unit 207 is configured to provide the necessary power to each of the components of the data processing unit 102 shown in FIG. 2.

Referring back to FIG. 2, the power supply section 207 of the data processing unit 102 in one embodiment may include a rechargeable battery unit that may be recharged by a separate power supply recharging unit (for example, provided in the receiver unit 104) so that the data processing unit 102 may be powered for a longer period of usage time. In certain embodiments, the data processing unit 102 may be configured without a battery in the power supply section 207, in which case the data processing unit 102 may be configured to receive power from an external power supply source (for example, a battery, electrical outlet, etc.) as discussed in further detail below.

Referring yet again to FIG. 2, a temperature detection section 203 of the data processing unit 102 is configured to monitor the temperature of the skin near the sensor insertion site. The temperature reading may be used to adjust the analyte readings obtained from the analog interface 201.

The RF transmitter 206 of the data processing unit 102 may be configured for operation in a certain frequency band, e.g., the frequency band of 315 MHz to 322 MHz, for example, in the United States. (The frequency band may be the same or different outside the United States. Further, in certain embodiments, the RF transmitter 206 is configured to modulate the carrier frequency by performing, e.g., Frequency Shift Keying and Manchester encoding, and/or other protocol(s). In certain embodiments, the data transmission rate is set for efficient and effective transmission. For example, in certain embodiments the data transmission rate may be about 19,200 symbols per second, with a minimum transmission range for communication with the primary receiver unit 104.

Also shown is a leak detection circuit 214 coupled to the guard contact (G) 211 and the processor 204 in the data processing unit 102 of the data monitoring and management system 100. The leak detection circuit 214 may be configured to detect leakage current in the sensor 101 to determine whether the measured sensor data is corrupt or whether the measured data from the sensor 101 is accurate. Such detection may trigger a notification to the user.

Figure 3:
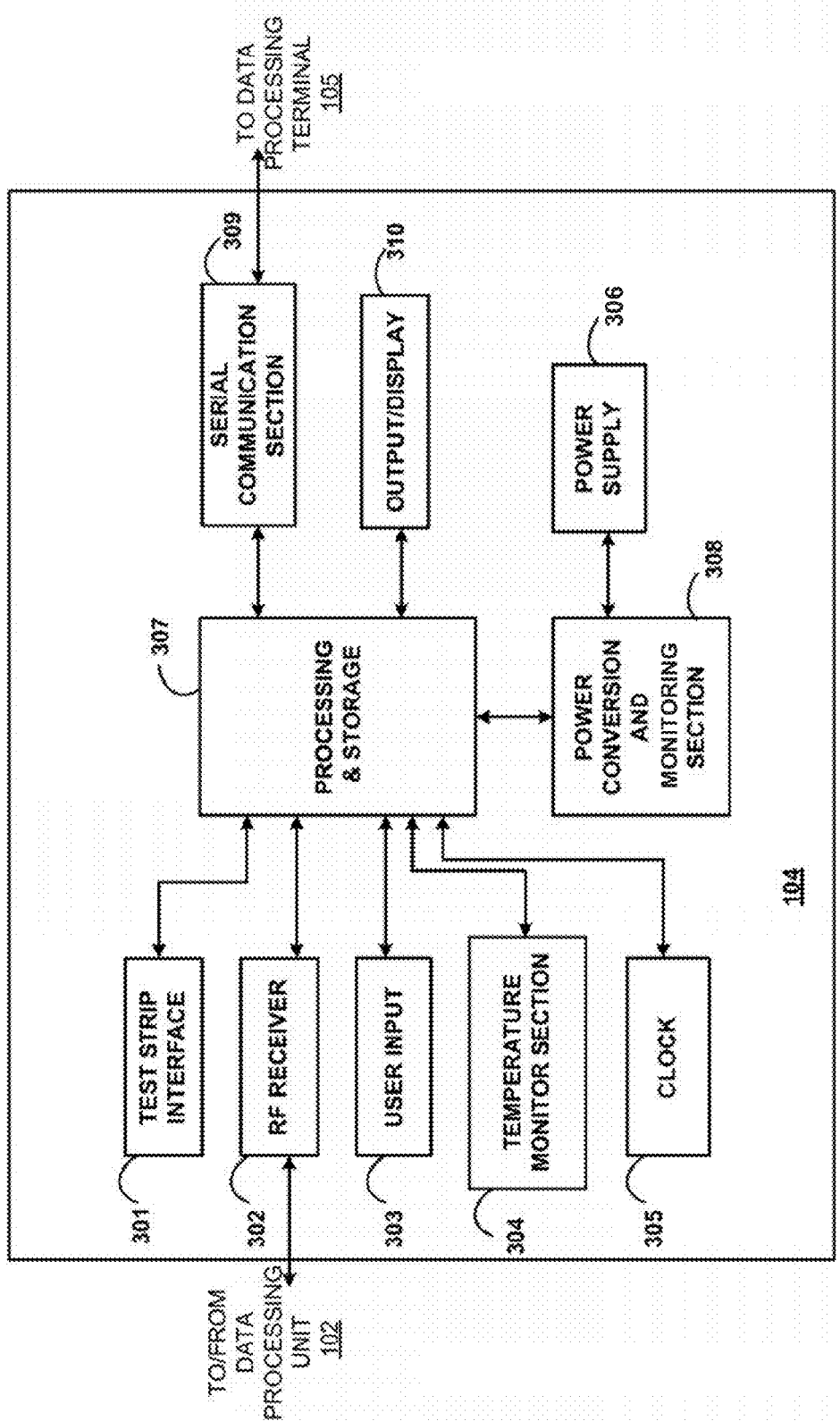
FIG. 3 shows a block diagram of an embodiment of the receiver/monitor unit of the data monitoring and management system of FIG. 1.

FIG. 3 is a block diagram of an embodiment of a receiver/monitor unit such as the primary receiver unit 104 of the data monitoring and management system shown in FIG. 1. The primary receiver unit 104 includes one or more of: a blood glucose test strip interface 301, an RF receiver 302, an input 303, a temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the processing and storage unit 307. The receiver may include user input and/or interface components or may be free of user input and/or interface components.

In certain embodiments, the test strip interface 301 includes a glucose level testing portion to receive a blood (or other body fluid sample) glucose test or information related thereto. For example, the interface may include a test strip port to receive a glucose test strip. The device may determine the glucose level of the test strip, and optionally display (or otherwise notice) the glucose level on the output 310 of the primary receiver unit 104. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. Freestyle® blood glucose test strips from Abbott Diabetes Care Inc. Glucose information obtained by the in vitro glucose testing device may be used for a variety of purposes, computations, and the like. For example, the information may be used to calibrate sensor 101, confirm results of the sensor 101 to increase the confidence thereof (e.g., in instances in which information obtained by sensor 101 is employed in therapy related decisions).

In further embodiments, the data processing unit 102 and/or the primary receiver unit 104 and/or the secondary receiver unit 106, and/or the data processing terminal/infusion section 105 may be configured to receive the blood glucose value wirelessly over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in the one or more of the data processing unit 102, the primary receiver unit 104, secondary receiver unit 106, or the data processing terminal/infusion section 105.

Additional detailed descriptions are provided in U.S. Pat. Nos. 5,262,035; 5,262,305; 5,264,104; 5,320,715; 5,593, 852; 6,103,033; 6,134,461; 6,175,752; 6,560,471; 6,579, 690; 6,605,200; 6,654,625; 6,746,582; 6,932,894; and in U.S. Published Patent Application No. 2004/0186365, the disclosures of each of which are herein incorporated by reference.

FIG. 4 schematically shows an embodiment of an analyte sensor in accordance with the present disclosure. This sensor embodiment includes electrodes 401, 402 and 403 on a base 404. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include but are not limited to aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The sensor may be wholly implantable in a user or may be configured so that only a portion is positioned within (internal) a user and another portion outside (external) a user. For example, the sensor 400 may include a portion positionable above a surface of the skin 410, and a portion positioned below the skin. In such embodiments, the external portion may include contacts (connected to respective electrodes of the second portion by traces) to connect to another device also external to the user such as a transmitter unit. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

FIG. 5A shows a perspective view of an embodiment of an electrochemical analyte sensor 500 having a first portion (which in this embodiment may be characterized as a major portion) positionable above a surface of the skin 510, and a second portion (which in this embodiment may be characterized as a minor portion) that includes an insertion tip 530 positionable below the skin, e.g., penetrating through the skin and into, e.g., the subcutaneous space 520, in contact with the user's biofluid such as interstitial fluid. Contact portions of a working electrode 501, a reference electrode 502, and a counter electrode 503 are positioned on the portion of the sensor 500 situated above the skin surface 510. Working electrode 501, a reference electrode 502, and a counter electrode 503 are shown at the second section and particularly at the insertion tip 530. Traces may be provided from the electrode at the tip to the contact, as shown in FIG. 5A. It is to be understood that greater or fewer electrodes may be provided on a sensor. For example, a sensor may include more than one working electrode and/or the counter and reference electrodes may be a single counter/reference electrode, etc.

FIG. 5B shows a cross sectional view of a portion of the sensor 500 of FIG. 5A. The electrodes 501, 502 and 503, of the sensor 500 as well as the substrate and the dielectric layers are provided in a layered configuration or construction. For example, as shown in FIG. 5B, in one aspect, the sensor 500 (such as the sensor 101 FIG. 1), includes a substrate layer 504, and a first conducting layer 501 such as carbon, gold, etc., disposed on at least a portion of the substrate layer 504, and which may provide the working electrode. Also shown disposed on at least a portion of the first conducting layer 501 is a sensing layer 508.

A first insulation layer such as a first dielectric layer 505 is disposed or layered on at least a portion of the first conducting layer 501, and further, a second conducting layer 509 may be disposed or stacked on top of at least a portion of the first insulation layer (or dielectric layer) 505. As shown in FIG. 5B, the second conducting layer 509 may provide the reference electrode 502, and in one aspect, may include a layer of silver/silver chloride (Ag/AgCl), gold, etc.

A second insulation layer 506 such as a dielectric layer in one embodiment may be disposed or layered on at least a portion of the second conducting layer 509. Further, a third conducting layer 503 may provide the counter electrode 503. It may be disposed on at least a portion of the second insulation layer 506. Finally, a third insulation layer 507 may be disposed or layered on at least a portion of the third conducting layer 503. In this manner, the sensor 500 may be layered such that at least a portion of each of the conducting layers is separated by a respective insulation layer (for example, a dielectric layer). The embodiment of FIGS. 5A and 5B show the layers having different lengths. Some or all of the layers may have the same or different lengths and/or widths.

In certain embodiments, some or all of the electrodes 501, 502, 503 may be provided on the same side of the substrate 504 in the layered construction as described above, or alternatively, may be provided in a co-planar manner such that two or more electrodes may be positioned on the same plane (e.g., side-by side (e.g., parallel) or angled relative to each other) on the substrate 504. For example, co-planar electrodes may include a suitable spacing there between and/or include dielectric material or insulation material disposed between the conducting layers/electrodes. Furthermore, in certain embodiments one or more of the electrodes 501, 502, 503 may be disposed on opposing sides of the substrate 504. In such embodiments, contact pads may be on the same or different sides of the substrate. For example, an electrode may be on a first side and its respective contact may be on a second side, e.g., a trace connecting the electrode and the contact may traverse through the substrate.

As noted above, analyte sensors may include an analyte-responsive enzyme to provide a sensing component or sensing layer. Some analytes, such as oxygen, can be directly electrooxidized or electroreduced on a sensor, and more specifically at least on a working electrode of a sensor. Other analytes, such as glucose and lactate, require the presence of at least one electron transfer agent and/or at least one catalyst to facilitate the electrooxidation or electroreduction of the analyte. Catalysts may also be used for those analyte, such as oxygen, that can be directly electrooxidized or electroreduced on the working electrode. For these analytes, each working electrode includes a sensing layer (see for example sensing layer 508 of FIG. 5B) proximate to or on a surface of a working electrode. In many embodiments, a sensing layer is formed near or on only a small portion of at least a working electrode.

The sensing layer includes one or more components designed to facilitate the electrochemical oxidation or reduction of the analyte. The sensing layer may include, for example, a catalyst to catalyze a reaction of the analyte and produce a response at the working electrode, an electron transfer agent to transfer electrons between the analyte and the working electrode (or other component), or both.

A variety of different sensing layer configurations may be used. In certain embodiments, the sensing layer is deposited on the conductive material of a working electrode. The sensing layer may extend beyond the conductive material of the working electrode. In some cases, the sensing layer may also extend over other electrodes, e.g., over the counter electrode and/or reference electrode (or counter/reference is provided).

A sensing layer that is in direct contact with the working electrode may contain an electron transfer agent to transfer electrons directly or indirectly between the analyte and the working electrode, and/or a catalyst to facilitate a reaction of the analyte. For example, a glucose, lactate, or oxygen electrode may be formed having a sensing layer which contains a catalyst, such as glucose oxidase, lactate oxidase, or laccase, respectively, and an electron transfer agent that facilitates the electrooxidation of the glucose, lactate, or oxygen, respectively.

Examples of sensing layers that may be employed are described in U.S. patents and applications noted herein, including, e.g., in U.S. Pat. Nos. 5,262,035; 5,264,104; 5,543,326; 6,605,200; 6,605,201; 6,676,819; and 7,299,082; the disclosures of which are herein incorporated by reference.

In other embodiments the sensing layer is not deposited directly on the working electrode. Instead, the sensing layer may be spaced apart from the working electrode, and separated from the working electrode, e.g., by a separation layer. A separation layer may include one or more membranes or films or a physical distance. In addition to separating the working electrode from the sensing layer the separation layer may also act as a mass transport limiting layer and/or an interferent eliminating layer and/or a biocompatible layer.

Exemplary mass transport layers are described in U.S. patents and applications noted herein, including, e.g., in U.S. Pat. Nos. 5,593,852; 6,881,551; and 6,932,894, the disclosures of which are herein incorporated by reference.

In certain embodiments which include more than one working electrode, one or more of the working electrodes may not have a corresponding sensing layer, or may have a sensing layer which does not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing layers by, for example, subtracting the signal.

In certain embodiments, the sensing layer includes one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes such as ferrocene. Examples of inorganic redox species are hexacyanoferrate (III), ruthenium hexamine, etc.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

One type of polymeric electron transfer agent contains a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, such as 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone (PQQ), dependent glucose dehydrogenase, flavine adenine dinucleotide (FAD), or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone (PQQ), dependent glucose dehydrogenase or oligosaccharide dehydrogenase, flavine adenine dinucleotide (FAD) dependent glucose dehydrogenase, nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent (which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

Certain embodiments include a Wired Enzyme™ sensing layer (Abbott Diabetes Care Inc.) that works at a gentle oxidizing potential, e.g., a potential of about +40 mV. This sensing layer uses an osmium (Os)-based mediator designed for low potential operation and is stably anchored in a polymeric layer. Accordingly, in certain embodiments the sensing element is a redox active component that includes (1) Osmium-based mediator molecules attached by stable (bidente) ligands anchored to a polymeric backbone, and (2) glucose oxidase enzyme molecules. These two constituents are crosslinked together.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating, etc.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over an enzyme-containing sensing layer and allowing the solution to cure for about one to two days or other appropriate time period. The crosslinker-polymer solution may be applied to the sensing layer by placing a droplet or droplets of the solution on the sensor, by dipping the sensor into the solution, or the like. Generally, the thickness of the membrane is controlled by the concentration of the solution, by the number of droplets of the solution applied, by the number of times the sensor is dipped in the solution, or by any combination of these factors. A membrane applied in this manner may have any combination of the following functions: (1) mass transport limitation, i.e., reduction of the flux of analyte that can reach the sensing layer, (2) biocompatibility enhancement, or (3) interferent reduction.

The electrochemical sensors may employ any suitable measurement technique. For example, may detect current or may employ potentiometry. Technique may include, but are not limited to amperometry, coulometry, voltammetry. In some embodiments, sensing systems may be optical, colorimetric, and the like.

In certain embodiments, the sensing system detects hydrogen peroxide to infer glucose levels. For example, a hydrogen peroxide-detecting sensor may be constructed in which a sensing layer includes enzyme such as glucose oxides, glucose dehydrogenase, or the like, and is positioned proximate to the working electrode. The sending layer may be covered by a membrane that is selectively permeable to glucose. Once the glucose passes through the membrane, it is oxidized by the enzyme and reduced glucose oxidase can then be oxidized by reacting with molecular oxygen to produce hydrogen peroxide.

Certain embodiments include a hydrogen peroxide-detecting sensor constructed from a sensing layer prepared by crosslinking two components together, for example: (1) a redox compound such as a redox polymer containing pendent Os polypyridyl complexes with oxidation potentials of about +200 mV vs. SCE, and (2) periodate oxidized horseradish peroxidase (HRP). Such a sensor functions in a reductive mode; the working electrode is controlled at a potential negative to that of the Os complex, resulting in mediated reduction of hydrogen peroxide through the HRP catalyst.

In another example, a potentiometric sensor can be constructed as follows. A glucose-sensing layer is constructed by crosslinking together (1) a redox polymer containing pendent Os polypyridyl complexes with oxidation potentials from about −200 mV to +200 mV vs. SCE, and (2) glucose oxidase. This sensor can then be used in a potentiometric mode, by exposing the sensor to a glucose containing solution, under conditions of zero current flow, and allowing the ratio of reduced/oxidized Os to reach an equilibrium value. The reduced/oxidized Os ratio varies in a reproducible way with the glucose concentration, and will cause the electrode's potential to vary in a similar way.

A sensor may also include an active agent such as an anticlotting and/or antiglycolytic agent(s) disposed on at least a portion of a sensor that is positioned in a user. An anticlotting agent may reduce or eliminate the clotting of blood or other body fluid around the sensor, particularly after insertion of the sensor. Examples of useful anticlotting agents include heparin and tissue plasminogen activator (TPA), as well as other known anticlotting agents. Embodiments may include an antiglycolytic agent or precursor thereof. Examples of antiglycolytic agents are glyceraldehyde, fluoride ion, and mannose.

Sensors may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, such as but not limited to glucose concentration and/or temperature and/or rate of change of glucose, etc.

Calibration may be accomplished using an in vitro test strip (or other reference), e.g., a small sample test strip such as a test strip that requires less than about 1 microliter of sample (for example FreeStyle® blood glucose monitoring test strips from Abbott Diabetes Care Inc.). For example, test strips that require less than about 1 nanoliter of sample may be used. In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is firstly obtained. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate. In certain embodiments, a system need only be calibrated once by a user, where recalibration of the system is not required.

Calibration and validation protocols for the calibration and validation of in vivo continuous analyte systems including analyte sensors, for example, are described in e.g., U.S. Pat. Nos. 6,284,478; 7,299,082; and U.S. patent application Ser. No. 11/365,340, now U.S. Pat. No. 7,885,698; Ser. No. 11/537,991, now U.S. Pat. No. 7,618,369; Ser. No. 11/618, 706; Ser. No. 12/242,823, now U.S. Pat. No. 8,219,173; and Ser. No. 12/363,712, now U.S. Pat. No. 8,346,335, the disclosures of each of which are herein incorporated by reference.

Analyte systems may include an optional alarm system that, e.g., based on information from a processor, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels approach, reach or exceed a threshold value. An alarm system may also, or alternatively, be activated when the rate of change, or acceleration of the rate of change, in analyte level increase or decrease approaches, reaches or exceeds a threshold rate or acceleration. A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

The embodiments of the present disclosure also include sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

As is well established, HbA1C (also referred to as A1C) is the standard metric for determining an individual's glycemic control. Studies have recently derived relationships of HbA1C to mean blood glucose levels. The advent of continuous glucose monitoring (CGM) has enabled accurate and continuous measurements of mean glucose levels over extended periods of time.

It has been shown that controlling HbA1C levels as close to a normal level as possible is important to reduce the risk of diabetic complications. However, it is generally difficult to achieve the tight glycemic control necessary to obtain the desired reduction in HbA1C levels without potentially increasing the risk of hypoglycemic condition. In one aspect, mean glucose values may be associated or correlated with the HbA1C levels. For example, a slope of 36 mg/dL per 1% HbA1C illustrates the relationship between the regression analysis relating HbA1C level to mean glucose values. Further, a lower slope of approximately 18 mg/dL may indicate the relationship between HbA1C level and mean glucose values. Additionally, variability may exist between diabetic patients as pertains to the relationship between the HbA1C level and mean glucose values, indicating a potentially individualized characteristic of the rate of protein glycation that may affect long term complications of poorly controlled diabetic condition. Other variables such as race and ethnicity also may have effect in the HbA1C level adjusted for glycemic indices.

Accordingly, embodiments of the present disclosure include improvement in the HbA1C level estimation with the knowledge or information of the patient's individualized relationship between HbA1C level and the mean glucose values.

In one aspect, a diabetic patient or a subject with a lower slope (showing the relationship between HbA1C level and mean glucose values) may be able to achieve a greater improvement in HbA1C level for a given decrease in average glucose levels, as compared with a patient with a higher slope. As such, the patient with the lower slope may be able to achieve a reduced risk of chronic diabetic complications by lower HbA1C level with a minimal increase in the risk of potentially severe hypoglycemia (due to a relatively modest reduction in the average glucose values in view of their lower slope).

Given the individualized information related to a patient's average glucose value relative to the HbA1C level, a physician or a care provider in one aspect may determine suitable glycemic targets for the particular patient such that the calculated reduction in the HbA1C level may be attained while minimizing the risk of severe hypoglycemia.

In one aspect, in the analyte monitoring system 100 (FIG. 1), a blood glucose meter or monitor with sufficient data capacity for storing and processing glucose values, or a data processing terminal 105 (FIG. 1) with data management capability such as, for example, CoPilot™ Health Management Software available from Abbott Diabetes Care Inc., of Alameda, Calif., may be configured to provide improved glycemic control based on mean glucose values and HbA1C levels. For example, in one aspect, an HbA1C measurement may be obtained either manually entered or downloaded from the patient's medical records, and an average glucose level is calculated over a predetermined time period (such as 30 days, 45 days, 60 days, 90 days and so on).

With the average glucose level information, a patient's individual relationship between average glucose and HbA1C (or other glycated proteins) may be determined. The determined individual relationship may be represented or output as a slope (lower slope or higher slope in graphical representation, for example), based upon a line fit to two or more determinations of average glucose and HbA1C, for example.

Alternatively, the individualized relationship may be based upon a single assessment of average glucose level and HbA1C and an intercept value, which may correspond to an HbA1C of zero at zero mean glucose level. Based on this, the physician or the health care provider (or the analyte monitoring device of data management software) may determine appropriate or suitable individualized glycemic targets to achieve the desired reductions in HbA1C without the undesired risk of severe hypoglycemia. In one aspect, the analysis may be repeated one or more times (for example, quarterly with each regularly scheduled HbA1C test) to update the glycemic targets so as to optimize therapy management and treatment, and to account for or factor in any intra-person variability.

In this manner, in one aspect, there is provided a systematic and individualized approach to establish and update glycemic targets based upon the relationship between the mean glucose values (as may be determined using a continuous glucose monitoring system or discrete in vitro blood glucose meter tests) and their HbA1C level, and a determination of an acceptable level of risk of severe hypoglycemia.

Accordingly, embodiments of the present disclosure provide individualized glycemic targets to be determined for a particular patient based upon their individualized rate of protein glycation, measured by the relationship between the mean glucose values and the HbA1C levels, such that the physician or the care provider, or the analyte monitoring system including data management software, for example, may determine the glycemic targets to achieve the desired reduction in HbA1C level without the unnecessary risk for hypoglycemic condition.

Additionally, based on the information or individualized relationship discussed above, embodiments of the present disclosure may be used to improve the estimation of subsequent HbA1C values based upon measured or monitored glucose values of a patient. In this manner the HbA1C level estimation may be improved by using the patient's individualized relationship between prior or past HbA1C levels, and mean glucose values to more accurately predict or estimate current HbA1C levels.

In this manner, in aspects of present disclosure, the HbA1C level estimation may be improved or enhanced based on a predetermined individualized relationship between a patient's average glucose values and their HbA1C and the current mean glucose level.

Experimental Study #1

Eighty eight (88) subjects used the FreeStyle Navigator® Continuous Glucose Monitoring (CGM) system over a 90 day period to obtain CGM system data and to perform discrete blood glucose measurements using the Freestyle® blood glucose meter built into the receiver of the CGM system for sensor calibration, confirmation of glucose related notifications or alarms, and insulin therapy adjustments. Threshold and projected alarms were enabled and subjects were not blinded to the real time monitored glucose data.

Mean CGM glucose data and self-monitoring of discrete blood glucose (SMBG) test readings were obtained over a 90 day period. The relationship between the mean glucose level and HbA1C level was determined for 88 subjects with Type 1 diabetes over this time period. Overall, 4.3±3.9 (mean±standard deviation (SD)) SMBG and 95.0±61.5 CGM readings were collected each day. Including only patient-days with at least one CGM (6194/7920) or SMBG (6197/7920) value, 5.4±3.5 SMBG and 121.5±40.2 CGM readings per day were obtained and available.

Equations for least-square linear regression fits of CGM and SMBG measurements to HbA1C were similar:

(mean glucose)=(slope±1$SE$)*$HbA1C$+
(intercept±1$SE$)

mean CGM[mg/dL]=20.5±2.1*$A1C$+5.2±14.7,
$r^2$=0.52 mean SMBG[mg/dL]=19.0±2.6*$A1C$+16.2±18.1,
$r^2$=0.38

These slopes of 19.0 and 20.5 (mg/dL)/% differ markedly from the American Diabetes Association (ADA) value of 35.6 (mg/dL)/%, but are similar to reports from recent studies using CGM data. Mean CGM and mean SMBG levels were found to be closely correlated:

mean CGM[mg/dL]=(0.80±0.04)*mean SMBG+
(27.9±6.4),$r^2$=0.80

The low slope of less than 1 for mean CGM data compared to mean SMBG levels may indicate the measurement selection bias of SMBG levels before and after meals and in response to CGM system alarms or notification. This bias did not greatly affect the relationship to HbA1C levels. However, mean CGM data correlated more closely to the HbA1C levels and thus a better indicator of the HbA1C level.

That the CGM data had an $r^2$ (Pearson's correlation coefficient) value of only 0.52 indicates that individual differences in rates of protein glycation at a given blood glucose concentration may be an important factor when addressing glycemic control. The individual differences may be relevant in determining risk of future diabetic complications, and may suggest personalized goals of mean glucose for a given HbA1C target.

Referring now to the Figures, FIG. 6 provides a tabular illustration of the demographic and characteristics of participants in the 90 days continuous glucose monitoring system use study in one aspect. As can be seen from the table shown in FIG. 6, the 88 subjects for the 90 day study were selected to cover a wide range of characteristics typical for the general population of people with diabetic conditions, and who generally have a controlled diabetic condition, with a maximum HbA1C level of 9.1%.

Figure 7:
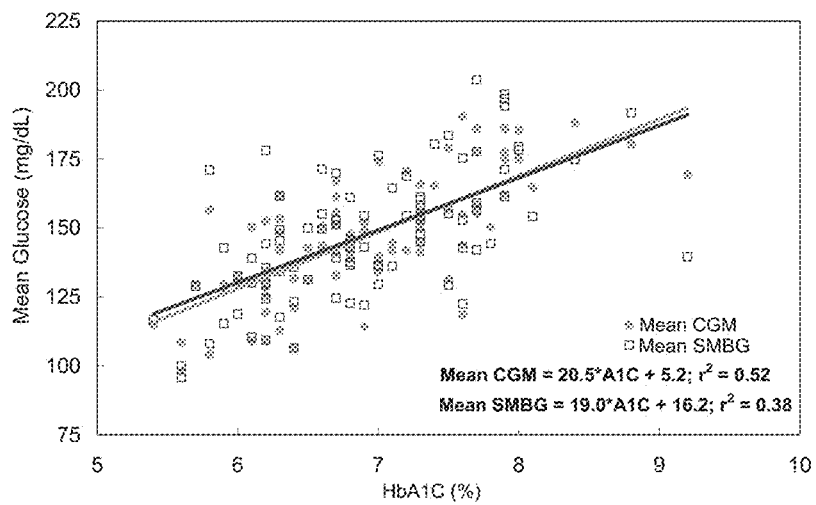
FIG. 7 is a chart illustrating the relationship between the mean 90 day continuously monitored glucose level and the mean 90 day discrete blood glucose test results compared with the HbA1C level in one aspect.

FIG. 7 is a chart illustrating the relationship between the mean 90 day continuously monitored glucose level and the mean 90 day discrete blood glucose test results compared with the HbA1C level in one aspect. Referring to FIG. 7, it can be seen that the CGM data and the SMBG readings were observed to have similar relationship to HbA1C levels, despite the less frequency of the SMBG readings. However, the level of the relationship to the HbA1C levels are relatively moderate, indicating other variables which may affect the relationship, including, for example, genetic factors that may impact the glycation of the hemoglobin molecule in the presence of glucose, or individuals may have longer or shorter average erythrocyte lifespans.

Referring to FIG. 7, those individuals whose glucose values are above the line of the mean relationship as shown can tolerate more glucose without increasing their HbA1C level, while those individuals whose glucose values are below the mean relationship line experience increases in HbA1C level at lower than expected blood glucose concentrations. In one aspect, the rate of glycation based on a 90 day (or some other suitable time range) mean glucose level divided by the HbA1C level may provide useful guidance in therapy decisions.

Figure 8:
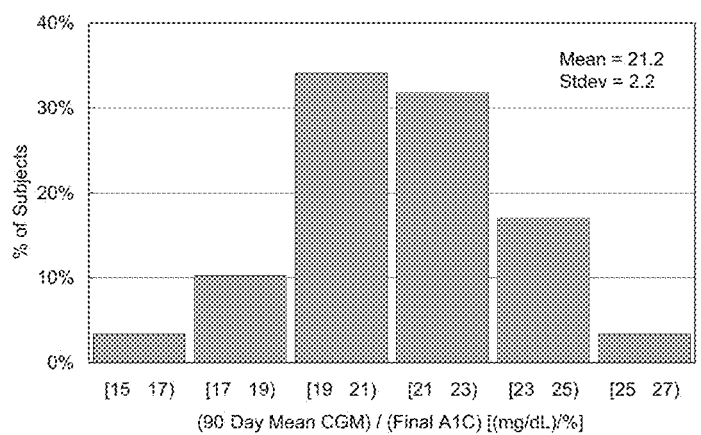
FIG. 8 provides a graphical illustration of the individual rates of glycation distribution in one aspect.

FIG. 8 provides a graphical illustration of the individual rates of glycation distribution in one aspect. Referring to FIG. 8, the rate of glycation including the 90 day mean glucose value divided by the HbA1C level characterizes an individual's sensitivity to changes in HbA1C level at a given blood glucose concentration. FIG. 8 illustrates the distribution of rates of glycation for the subjects in the study. As shown, approximately 15% of the participants may be considered "sensitive glycators" with a glycation ratio of approximately 19 or less. These individuals would need to maintain their blood glucose level to a lower-than-average value to maintain relatively the same HbA1C level as other individuals. For example, if the glycation ratio is 15, than the mean blood glucose level must be kept at approximately 75 mg/dL to expect and HbA1C level of approximately 5%.

Referring again to FIG. 8, approximately 22% of the study participants may be considered "insensitive glycators" with a glycation ratio of approximately 23 or more. That is, these insensitive glycators may keep their blood glucose higher-than-average level and maintain approximately the same HbA1C level as other individuals. For example, if the glycation ratio is 25, then the mean blood glucose level can be maintained at approximately 125 mg/dL to expect an HbA1C level of approximately 5%.

Figure 9:
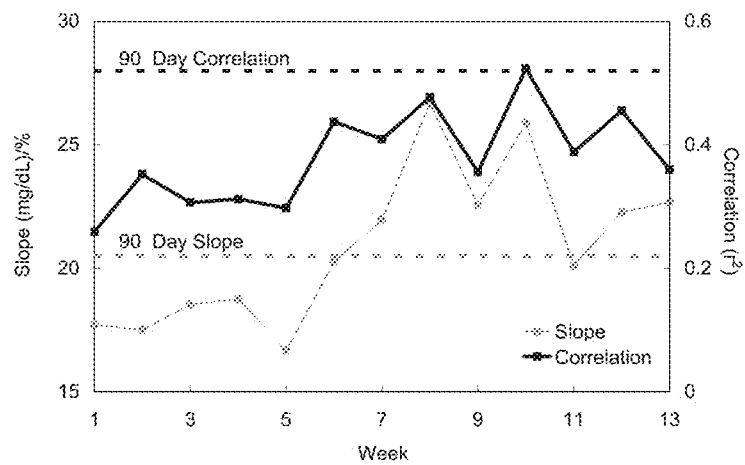
FIG. 9 provides a graphical illustration of the slope and correlation of the continuously monitored glucose level to the HbA1C level on a weekly basis in one aspect.

FIG. 9 provides a graphical illustration of the slope and correlation of the continuously monitored glucose level to the HbA1C level on a weekly basis in one aspect. HbA1C is considered to be the weighted average of blood glucose levels for the 90 day period based on the average lifespan of erythrocytes. The weighted average, however, may or may not be a linear relationship. More recent blood glucose levels may influence the HbA1C level more strongly (thus weighting more heavily) than the more distant (in time) blood glucose levels. FIG. 9 illustrates the Pearson's correlation (r2) and linear regression slope for each of the 12 weeks prior to the HbA1C measurement. The horizontal lines as shown in the Figure illustrate the values when all weeks in the study are pooled together. From FIG. 9, it can be seen that the more recent weeks (for example, weeks 6 to 13) have a stronger influence on HbA1C level (that is, a having a higher correlation and slope) than the more distant weeks (for example weeks 1 to 5).

Figure 10:
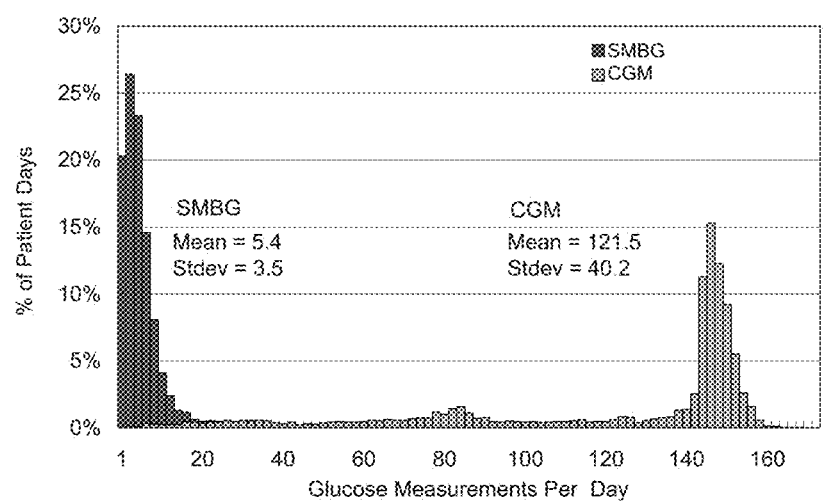
FIG. 10 is a graphical illustration of the frequency of the obtained glucose levels between the SMBG (self monitored blood glucose) measurements and the CGM (continuously monitored glucose) measurement on a daily basis in one aspect.

FIG. 10 is a graphical illustration of the frequency of the obtained glucose levels between the SMBG (self monitored blood glucose) measurements and the CGM (continuously monitored glucose) measurement on a daily basis in one aspect. That is, the episodic measurements (SMBG) compared to the continuous measurements (CGM) in the study are shown in the Figure. The frequency of the glucose levels per day is shown for the two measurements. As can be seen, on average, 5.4 SMBG measurements were performed per day (e.g., once per 4.4 hours) compared to 121.5 CGM measurements per day (once per 12 minutes).

Figure 11:
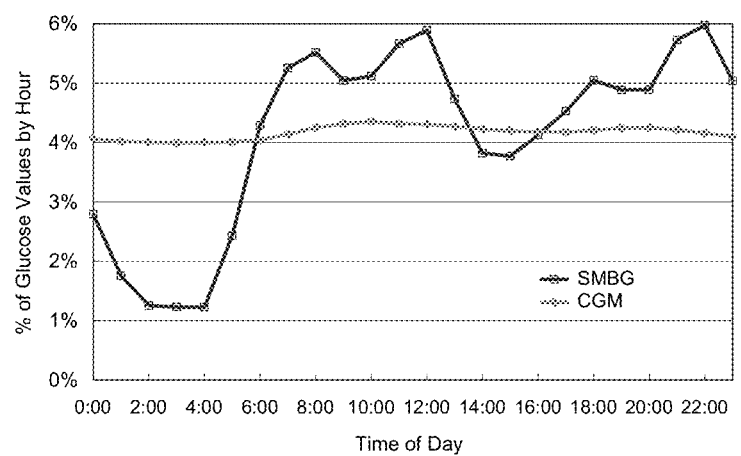
FIG. 11 is a graphical illustration of the glucose measurement distribution by time of day between the SMBG (self monitored blood glucose) measurements and the CGM (continuously monitored glucose) measurement in one aspect.

FIG. 11 is a graphical illustration of the glucose measurement distribution by time of day between the SMBG (self monitored blood glucose) measurements and the CGM (continuously monitored glucose) measurement in one aspect. As shown in FIG. 11, on average, it can be seen that the SMBG measurements were performed during the day, with spikes near typical meal times, as compared to substantially steady continuous CGM measurements.

Experimental Study #1 Results

Based on data collected over the 90 day period, the following observations and results were determined. A correlation between HbA1C and mean glucose was observed, consistent with the indication that HbA1C level reflects the integral of blood glucose level over time. Similar slopes for the linear regression fits of CGM data and SMBG measurements to HbA1C of 20.5 and 19.0 (mg/dL)/%, respectively were observed. Further, both slopes were lower than the 35.6 (mg/dL)/% from HbA1C values paired with 7-point profiles from 1,439 subjects, but consistent with other studies using CGM data. Moreover, the weaker correlation of mean glucose level to HbA1C with SMBG values indicates that infrequent and inconsistently timed glucose measurements (SMBG) may not accurately reflect glucose concentrations over time as well as CGM data. Additionally, the results indicate an inter-individual variability in glycation rates or erythrocyte survival.

This study of 88 subjects with Type 1 diabetes mellitus and widely varying HbA1C levels demonstrated a strong correlation between CGM data averaged over the preceding 90 days and HbA1C level. Study subjects were compliant, using the FreeStyle Navigator® Continuous Glucose Monitoring System on greater than 78% of study days and logging an average of 121.5 CGM readings per day (CGM readings recorded every 10 minutes) on days with at least one CGM value.

Results from the studies have demonstrated that the rate of microvascular complications is correlated with HbA1C levels. Re-analysis of this data also indicates that mean glucose is correlated with macrovascular complications. Whereas real-time monitored CGM data may significantly improve the management of diabetes through the availability of glucose values, trend indicators, and alarms/alerts, it may be also used for the determination of mean glucose level and for the prediction of HbA1C level. These metrics have been shown to track long-term complications and are essential for physiological condition or therapy management.

Improved understanding of inter- and intra-individual variation in the relationship between mean glucose level and HbA1C level may be useful in the determination of glucose targets designed to optimize both the reduction in an individual's risk of the long-term complications of diabetes and their short-term risk of hypoglycemia. For example, patients with different relationships between mean glucose and HbA1C may be able to achieve similar reductions in the risk of microvascular complications of diabetes with markedly different decreases in mean glucose, with those patients with the lowest ratios of mean glucose to HbA1C experiencing the least risk of hypoglycemia.

Experimental Study #2

In this experimental study, the objective was to assess glucose control. Threshold and projected alarms were enabled and subjects were not blinded to the glucose data. HbA1C measurements were obtained at the beginning of the study and at the end of the study.

Data collected from the use of FreeStyle Navigator® Continuous Glucose Monitoring System was evaluated under home use conditions. In this multi-center study 90 subjects with Type 1 diabetes wore the continuous glucose monitor (CGM) for 3 months. Fifty-six percent of the subjects were female and the average age was 42 years (range 18-72). At baseline, 38% of the subjects had HbA1C values <7.0%.

Questionnaires were completed at baseline, day 30 and day 90. Subjects were provided with no additional therapeutic instructions other than to make treatment decisions based on confirmatory blood glucose tests. HbA1C was measured by a central laboratory at baseline and 90 days. One-minute continuous glucose values were used to assess the glycemic profiles of study subjects.

Subjects were trained in a clinic visit of approximately 2 hours. Ninety-nine percent reported being confident in CGM use based on the training Subjects inserted the sensors in the arm or abdomen with the most common adverse symptom being insertion site bleeding (59 episodes in 22 subjects). After 90 days, 92% reported an overall positive system experience. The most important system features to the study subjects were the glucose readings, glucose alarms and trend arrows.

Both subjects with baseline HbA1C≥8% (p=0.0036) and subjects with baseline HbA1C<8% (p=0.0001) had significant decreases in their HbA1C value after 90 days. The mean A1C decrease for subjects with baseline values of ≥8% was three times greater (−0.6%) than that of the subjects with baseline values of <8% (−0.2%; p=0.004).

After 90 days, 73% of subjects reported viewing the CGM data display more than 12 times per day. There was a direct correlation between subject's display reviews per day and corresponding HbA1C change. The improvement in glucose control was reflected in HbA1C changes after 90 days of CGM use with 55% of subjects reaching a target HbA1C value of <7.0%. The more frequently the patients viewed their glucose results, in general, the greater the improvement in HbA1C values. At baseline the subjects with an HbA1C of <7.0% had characteristics similar to those of subjects with an HbA1C of ≥7.0% (Table 1). Eight-nine (89) percent of the subjects were Caucasian. Most subjects (72%) had completed a 4-year college degree.

Figures 12, 13:
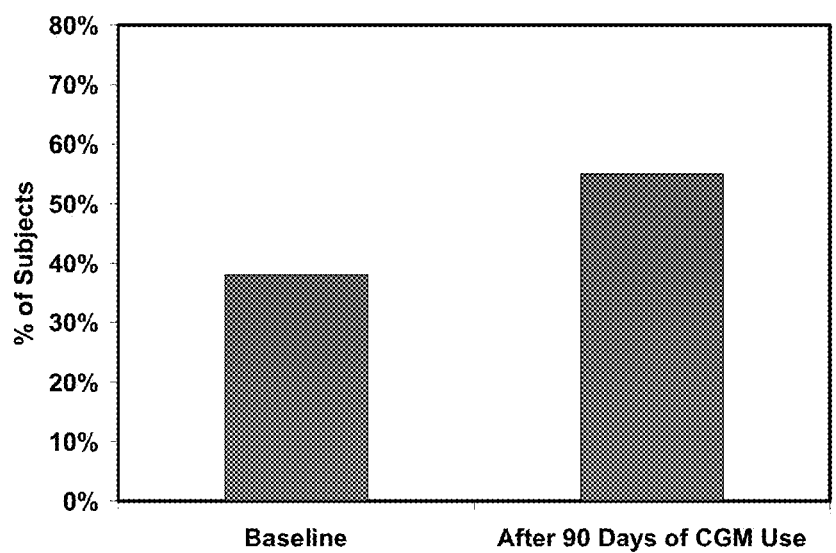
FIG. 12 is a tabular illustration of the study subject characteristics by baseline HbA1C level in one aspect.
FIG. 13 is a graphical illustration of the increase in the number of study subjects that achieved in-target HbA1C during the 90 day study duration in one aspect.

Referring now to the Figures, FIG. 12 is a tabular illustration of the study subject characteristics by baseline HbA1C level in one aspect. It can be seen from FIG. 12 that the participants of the study had an initial in-target (defined by the American Diabetes Association (ADA)) HbA1C level of <7%, where similar in gender, age, BMI (body mass index), and diabetes duration, compared to the participants in the study who had an above-target HbA1C level of >7% at the beginning of the study.

FIG. 13 is a graphical illustration of the increase in the number of study subjects that achieved in-target HbA1C during the 90 day study duration in one aspect. Referring to FIG. 13, it can be observed that during the 90 day study duration, the number of participants able to achieve an in-target HbA1C level increased from approximately 40% to approximately 57%.

Figure 14:
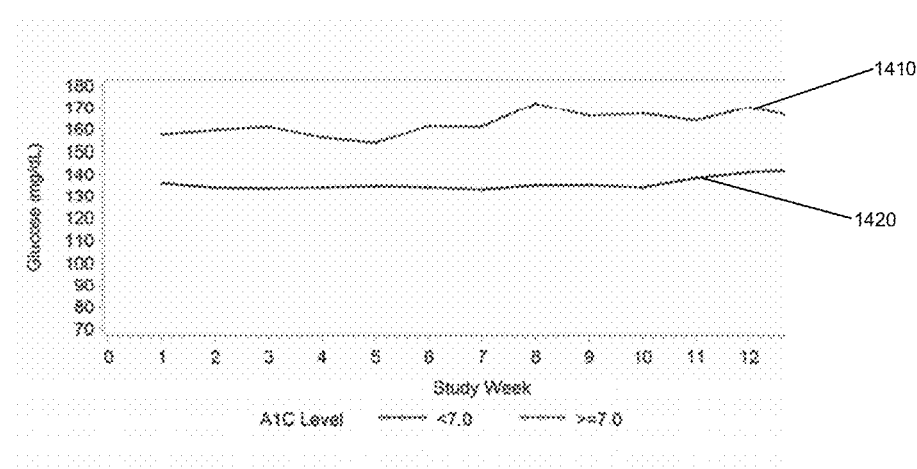
FIG. 14 is a graphical illustration of the difference between the mean glucose level of subjects with in-target HbA1C level compared to above-target HbA1C level during the study duration of 90 days in one aspect.

FIG. 14 is a graphical illustration of the difference between the mean glucose levels of subjects with in-target HbA1C level (1420) compared to above-target HbA1C level (1410) during the study duration of 90 days in one aspect. Referring to FIG. 14, during the 90 day study period, the participants with the initial in-target HbA1C level (1420) (as discussed above) had a lower mean glucose level than those with an initial above-target HbA1C level (1410). The weekly mean glucose level remained relatively stable for these participants with the initial in-target HbA1C level (1420), as compared with the participants with an above target HbA1C level (1410) whose weekly mean glucose level was relatively higher and increased towards the end of the 90 day study period.

Figure 15:
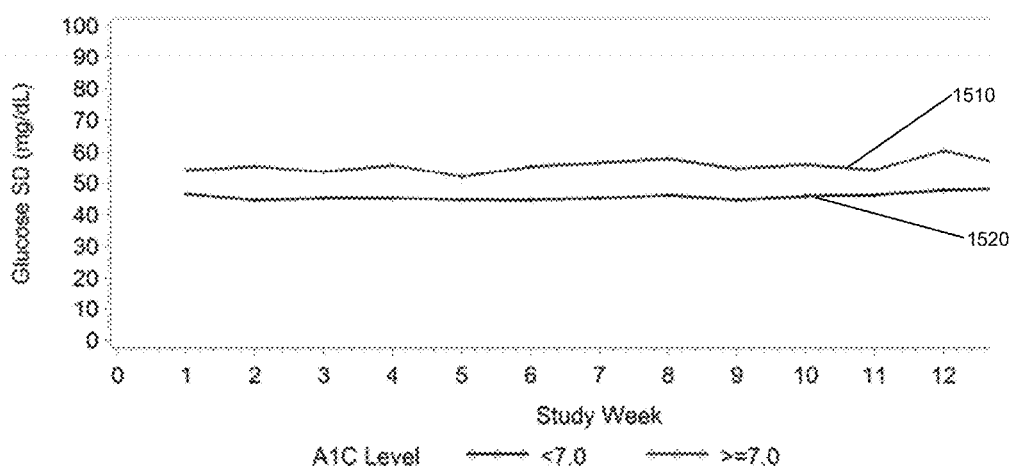
FIG. 15 is a graphical illustration of the glucose variation between subjects with in-target HbA1C level compared to above-target HbA1C level during the study duration of 90 days in one aspect.

FIG. 15 is a graphical illustration of the glucose variation between subjects with in-target HbA1C level (1520) compared to above-target HbA1C level (1510) during the study duration of 90 days in one aspect. It can be seen from FIG. 15 that during the study duration, the participants who had initial in-target HbA1C level (1520) had a lower glucose variation (measured by standard deviation per week), than those with an above-target HbA1C level (1510), and the glucose values remained relatively stable over study period.

Figure 16:
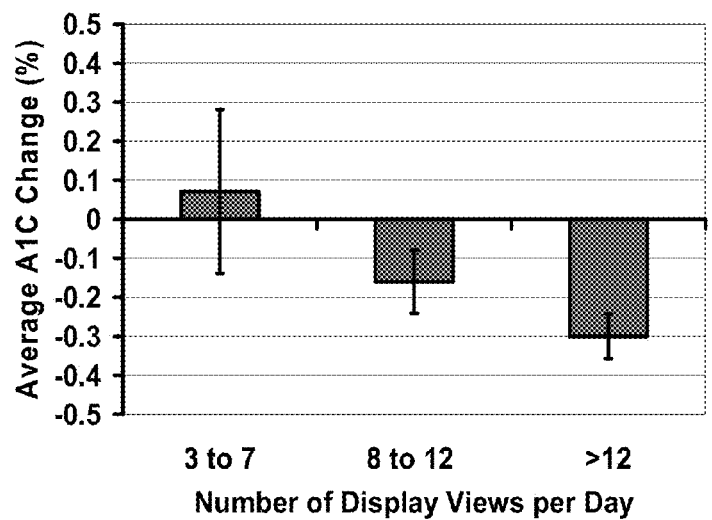
FIG. 16 is a graphical illustration of the average percentage HbA1C level change based on the number of times the study subjects viewed the continuously monitored glucose level in one aspect.

FIG. 16 is a graphical illustration of the average percentage HbA1C level change based on the number of times the study subjects viewed the continuously monitored glucose level in one aspect. It can be seen from FIG. 16 that the average change in HbA1C level during the 90 day study period for the participants as correlated with the number of times per day the participants reported viewing or seeing the real time CGM data display. It can be observed that the participants that were viewing the monitored glucose levels had their HbA1C levels reduced relatively more than those who viewed the monitored glucose levels less frequently.

Figure 17:
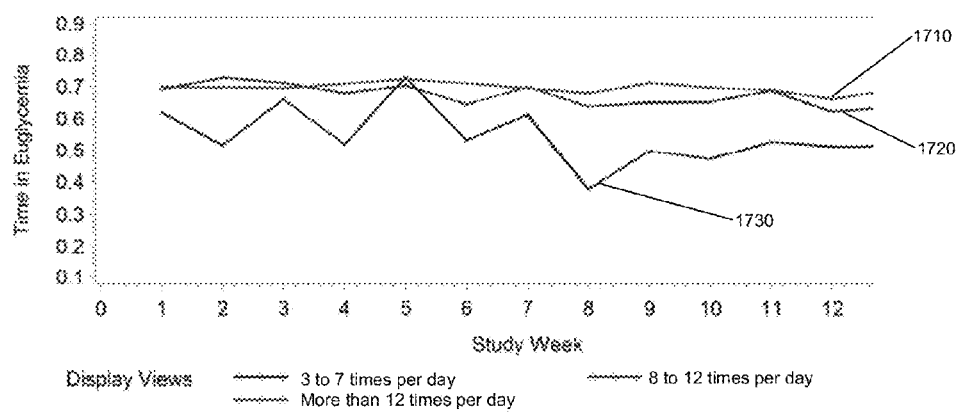
FIG. 17 graphically illustrates the weekly glycemic control results based on the number of times daily the subjects viewed the real time continuously monitored glucose levels in one aspect.

It can be seen that over the course of the 90 day study period using the CGM system, subjects/participants who reported viewing the display screen more frequently tended to have more improvement in HbA1C (FIG. 16), consistent with the time spent in euglycemia and glucose standard deviation demonstrated during the study (see, e.g., FIGS. 17-18).

FIG. 17 graphically illustrates the weekly glycemic control results based on the number of times daily the subjects viewed the real time continuously monitored glucose levels in one aspect. Referring to FIG. 17, the graphical illustration provides the glycemic control (i.e., measured as the percentage of time between 70 to 180 mg/dL) per week for participants associated with the number of times per day the participants reported viewing or looking at the continuously monitored real time glucose (CGM) data. It can be observed that the participants that viewed the glucose data less frequently (1730) had relatively more degraded glycemic control, with approximately 60% of the time spend in euglycemia condition during the first week of the study, down to approximately 50% of time spend in euglycemia in the last week, compared with the participants that viewed the glucose data more frequently (1710, 1720).

FIG. 18 is a graphical illustration of the glycemic variability measured as the standard deviation on a weekly basis of the subjects between the number of times daily the subjects viewed the real time continuously monitored glucose levels in one aspect. Again, it can be observed that based on the glycemic variability per week associated with the number of times per day they reported viewing or looking at the CGM data as shown in FIG. 18, the participants that viewed the real time glucose data less frequently had degraded glycemic variability (1830), compared with the participants that viewed the glucose data more frequently (1810, 1820).

Experimental Study #2 Results

Based on the foregoing, it can be observed that improvement in glucose control resulted in HbA1C changes after 3 months of CGM system use. For example, subjects/participants that reported viewing the display screen more frequently trended toward having greater improvement in HbA1C level. Although subjects were not provided therapeutic instruction in CGM, the glucose levels recorded throughout the study were consistent with the final HbA1C values.

FIG. 19 is a tabular illustration of three hypothetical subjects to evaluate and modify target continuously monitored glucose levels based on HbA1C measurements, average 30 day CGM data, and percentage of duration in hypoglycemic condition (<70 mg/dL) over the 30 day period in one aspect. As shown, patient 1 may be considered a "sensitive glycator" (see, e.g., FIG. 8) with a glycability ratio of 17. Also, it can be seen that the rate of hypoglycemia is relatively high. Thus, a therapy recommendation or compromise may include a target predicted HbA1C level of 6.5% which, for the sensitive glycator may translate to an average CGM level of 113 mg/dL. Referring to FIG. 19, patient 2 profile is similar to patient 1, but is not quite as sensitive a glycator, and thus, the CGM target may be at 118 mg/dL, with a predicted or anticipated HbA1C level of 6.0% (which is considered to be still "in-target"). Patient 3 as shown, may be considered an "insensitive glycator" and has a very low rate of hypoglycemia. Thus, despite having an in-target HbA1C of 6.1%, the recommended therapy management may include a more controlled HbA1C level of 5.5% corresponding to an average CGM level of 142 mg/dL.

For example, Patient A may begin at an HbA1C of 8.0%. He may be knowledgeable about food-insulin balancing and mealtime glucose corrections, but still feels overwhelmed by mealtime decisions. Looking at HbA1C and CGM data summary, Patient A's health care provider (HCP) sees that at meal times he has the following characteristics:

HbA1C=8.0
Starting meals in target 53% of the time
Staying in target for 40% of those
Moving into target 33% of the time when starting out of target The HCP may recommend continuing to focus on starting meals in target and staying there, and to maintain the rest of the therapy practices. Three months later, Patient A returns with these glucose metrics:

HbA1C=7.6
Starting meals in target 64% of the time
Staying in target for 53% of those
Moving into target 29% of the time when starting out of target It can be seen that Patient A's HbA1C level is closer to target, and improving in the areas that Patient A focussed on for the prior 3 months. At this point, the HCP recommends that glucose corrections at mealtimes should be the priority, while maintaining the rest of the therapy decisions. Patient A gets further training in mealtime corrections. As the months progress, Patient A improves mealtime glucose and has the following glucose metrics:

HbA1C=6.9
Starting meals in target 65% of the time
Staying in target for 60% of those
Moving into target 59% of the time when starting out of target It can be seen that Patient A's HbA1C is now in target, and Patient A and the HCP decide to maintain the therapy practices for the next few months.

Accordingly, embodiments of the present disclosure provide determination of individualized HbA1C target levels based on mean glucose values as well as other parameters such as the patient's prior HbA1C levels (determined based on a laboratory result or by other ways) to improve glycemic control. Furthermore, other metrics or parameters may be factored into the determination of the individualized HbA1C target level such as, for example, conditions that may be relevant to the patient's hypoglycemic conditions including patient's age, hypoglycemia unawareness, whether the patient is living alone or in assisted care, or with others, history hypoglycemia, whether the patient is an insulin pump user, or is under insulin or other medication therapy, the patient's activity levels and the like.

Additionally, other parameters may also include different or variable weighing functions to determine the mean glucose values, based on, for example, the time of day, or time weighted measures, and the like. Furthermore, the determination of the individualized HbA1C target level may also include patient specific relationship between HbA1C and mean glucose values, including the rate of glycation, erythrocyte lifespan, among others. Also, embodiments may include weighing functions or parameters based on the patient's risk of high and low blood glucose levels.

In accordance with the embodiments of the present disclosure, the individualized HbA1C target level may be provided to the patient in real time or retrospectively, and further, one or more underlying therapy related parameters may be provided to the patient or programmed in an analyte monitoring system such as, for example, but not limited to the receiver unit 104 of the analyte monitoring system 100 (FIG. 1). In this manner, therapy management settings, for example, on the receiver unit 104 such as alarm threshold settings, projected alarm sensitivities, target glucose levels, modification to insulin basal level, recommendation of a bolus intake, and the like may be presented to the patient or provided to the patient's healthcare provider to improve the patient's therapy management.

The illustrations below provide some non-limiting examples of determining an individual's glycemic targets based on the individual differences in glycability.

Figure 20:
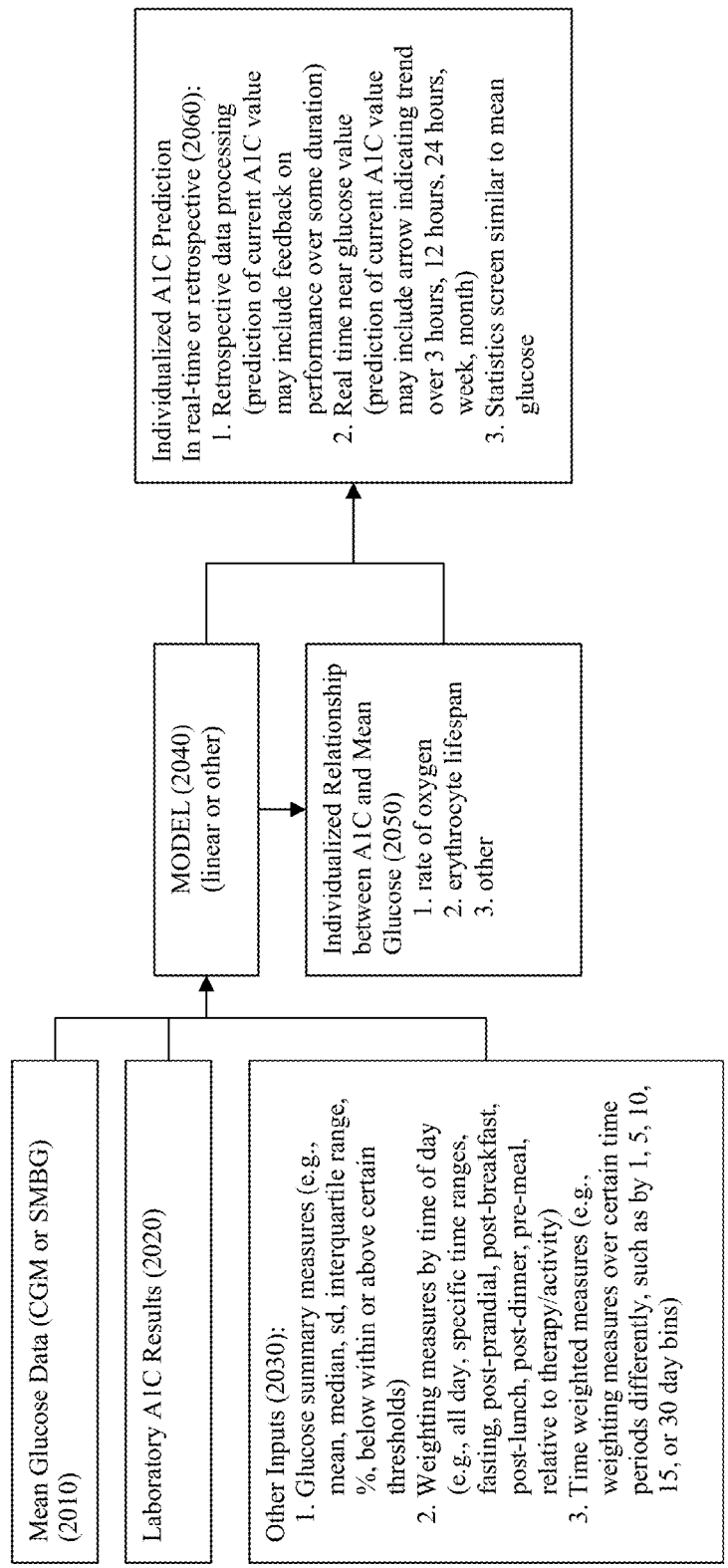
FIG. 20 illustrates routines for managing diabetic conditions based on HbA1C level and mean glucose data in one aspect.

FIG. 20 illustrates routines for managing diabetic conditions based on HbA1C (also referred to as A1C) level and mean glucose data in one aspect. Referring to FIG. 20, in one aspect, with the mean glucose data (CGM or SMBG) (2010) and laboratory determined HbA1C results (2020), a linear or nonlinear model (2040) may be applied to the glucose data (2010) and the HbA1C data (2020) in conjunction with the individualized relationship or correlation between the mean glucose data and the HbA1C data (2050). In one aspect, the individualized relationship or correlation (2050) may include, but is not limited to, the rate of glycation, and/or the erythrocyte lifespan, for example, among others.

As shown in the Figure, based on the model (2040) applied in conjunction with the determined relationship between the mean glucose level and HbA1C level (2050), individualized HbA1C level may be determined either in real time, or retrospectively (2060). For example, using a retrospective data management system based on one or more data processing algorithms or routines, for example, based on the CoPilot™ system discussed above, determination of future or prediction of current HbA1C level may be ascertained based, for example, on feedback on performance over a predetermined time duration, such as 30 days, 45 days, 60 days, 90 days, and so on. In a further aspect, the individualized HbA1C level determination may be performed in real time, based on real time CGM data, with trend arrows or indicators on the CGM system reflecting a trend or glucose data rate of change over a 3 hour, 12 hours, 24 hours, weekly, or monthly time period, or other suitable time frame.

Referring back to FIG. 20, it can be seen that, in a further aspect, in addition to the mean glucose data (2010) and the laboratory HbA1C level (2020), other input parameters (2030) may be provided to add robustness to the system. Examples of other input parameters include, for example, but not limited to glucose summary measures, weighting measures by time of day, time weighted measures, and others. For example, in one aspect, glucose summary measures may include mean, median, standard deviation, interquartile range, median percentage, below, within or above certain thresholds. Also, in one aspect, the weighting measures by time of day may include, for example, all day, specific time ranges, such as ±1 hour of a meal event, ±2 hours of a meal event, ±1 hour of an exercise event, ±2 hours of an exercise event, etc., fasting time period, post-prandial time period, post-breakfast time, post lunch time, post dinner time, pre-meal time, as well as post breakfast/lunch/dinner time relative to therapy administration and/or activity and the like. Additionally, the time weighted measures may include, in one aspect, weighted measures over predetermined time periods spaced, for example, differently, such as by, 1, 5, 10, 15, or 30 day bins.

Figure 21:
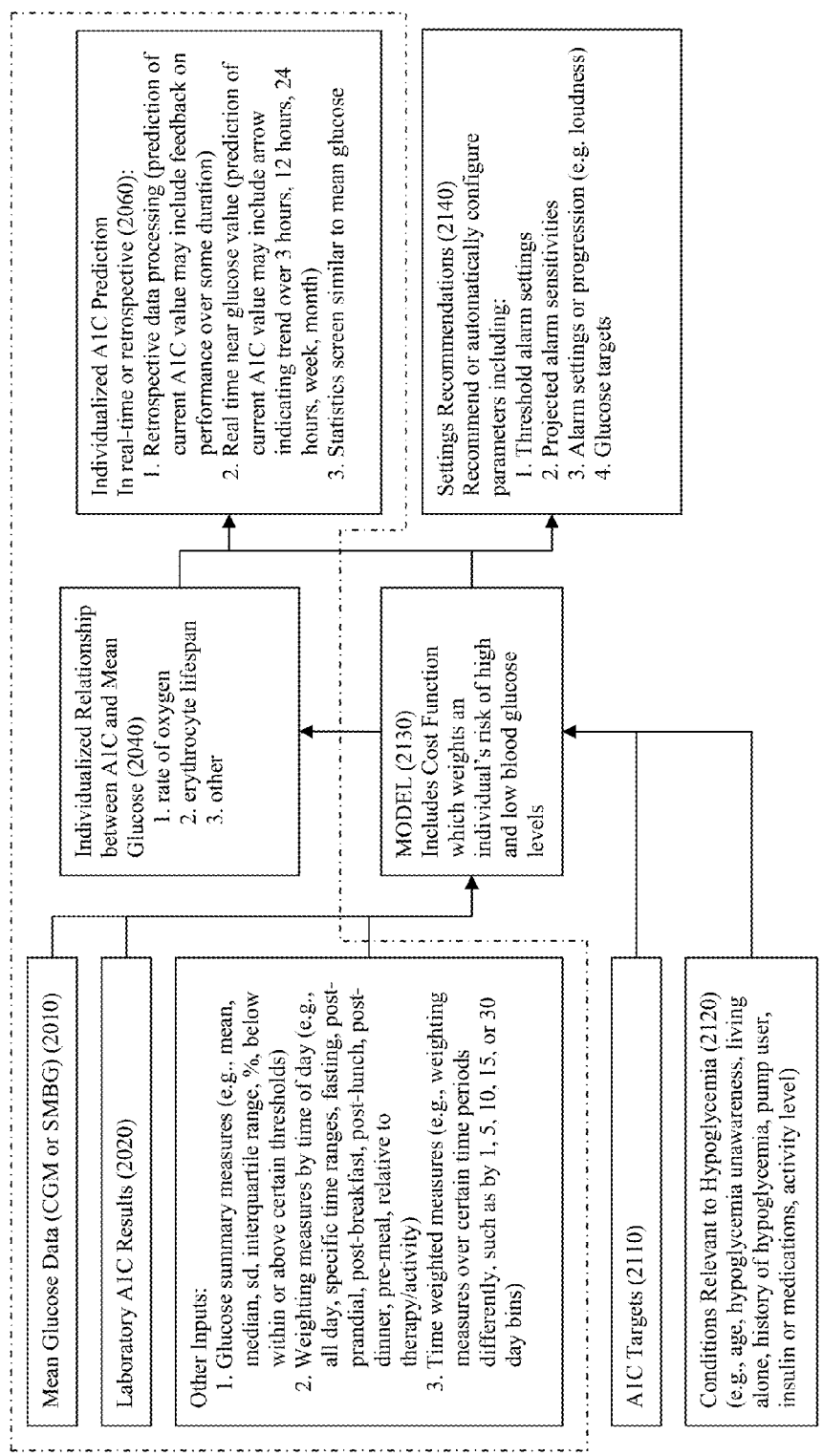
FIG. 21 illustrates routines for managing diabetic conditions based on HbA1C level and mean glucose data in another aspect.

FIG. 21 illustrates routines for managing diabetic conditions based on HbA1C level and mean glucose data in another aspect. Compared to the illustration provided in FIG. 20, in embodiments shown in FIG. 21, the linear/nonlinear model may include a cost function (2130) which may be configured to weigh an individual's risk of high and/or low blood glucose levels, in addition to accepting or factoring other input parameters, such as, for example, HbA1C level targets (2110) and/or conditions associated or relevant to hypoglycemia (2120). In one aspect, conditions relevant to hypoglycemia provided as one or more input parameters includes, for example, age, hypoglycemia unawareness, living conditions (e.g., living alone), history of hypoglycemia, insulin pump user, frequency or manner of insulin or medication ingestion or administration, activity level, among others.

Referring to FIG. 21, based on the input parameters provided to the model function, a further output or results in addition to the individualized HbA1C level determination or prediction, may include device or CGM system settings recommendation (2140) including, for example, glucose level threshold alarm settings, projected alarm sensitivities associated with the monitored glucose values, alarm settings or progression (e.g., increasing loudness/softness/strength in vibration, etc.), glucose level target levels, and the like. In accordance with aspects of the present disclosure, the setting recommendations (2140) or output may include treatment recommendations such as, for example, insulin/medication dosage information and/or timing of administration of the same, information or recommendation related to exercise, meals, consultation with a healthcare provider, and the like.

Experimental Study and Results #3

In a 90-day, 90-subject home use study of the FreeStyle Navigator® continuous glucose monitoring (CGM) system, participants were instructed on the built-in electronic logbook feature to indicate meals. While not required to record meals, the study resulted in 3,679 analyzable mealtime glucose profiles for 37 participants when at least 30 meal profiles per subject were required. This data was retrospectively analyzed to assess mealtime glucose relative to established glucose targets, define per-subject summary mealtime glucose parameters, and discern summary parameters for subjects of different A1C levels.

Overall, the subjects had an average HbA1C level of 7.1% (SD=0.82%, min/max=5.6/9.2%), and were in target either before or after meals according to ADA guidelines (90-130 mg/dL premeal, <180 mg/dL peak postmeal) for 31% and 47% of meals, respectively. Only 20% of all meals were in target both before and after meals. On a per subject basis, the results indicate a correlation between HbA1C levels and mealtime glucose control, and CGM system use illustrates trends and patterns around meals that differentiated those with higher and lower HbA1C values. Those subjects with the lowest HbA1C were able to most consistently achieve three patterns around meals: 1) start the meal in target, 2) stay in target postmeal, and 3) correct to in-target levels postmeal if the premeal value is out-of-target. Consistent use of the CGM system combined with health-care professional guidance for learning strategies to manage mealtime glucose patterns has promise for improving therapy choices and glucose control.

In this manner, in one aspect, summary and assessment of glucose control around meals may be determined that can be effectively understood and acted upon by analyte monitoring system users and their health care providers.

Mealtime therapy decisions are complex, as there are many interacting variables or complications to arriving at a decision that will result in good glucose level control. At each meal, there may be different factors such as: (1) time, amount and nutrient content to be consumed, (2) accuracy of the consumed nutrient content estimation (i.e. "carbohydrate counting"); (3) current state of health (sickness, menses, stress, other medications); (4) current amount of "insulin on board"; (5) recent prior activity level (exercising vigorously or not); (6) current glucose level; (7) current glucose trend ("rate of change", (mg/dL)/min); (8) maximum glucose after the meal; (9) minimum glucose after the meal; or (10) glucose at some timepoint after the meal (i.e. 2 hours).

In addition, there are individual factors to add to the complexity of determining a suitable treatment option including, for example, time-of-day dependent insulin-to-carbohydrate ratio, and/or time-of-day dependent insulin sensitivity ratio.

As an individual and his or her health care provider (HCP) become more informed about the value and variation of these parameters, HbA1C level, monitored CGM level and meal times can be used to guide therapy modification and training choices. These factors may be related to CGM data and summarized for different HbA1C levels to guide therapy adjustments and training.

Figure 22:
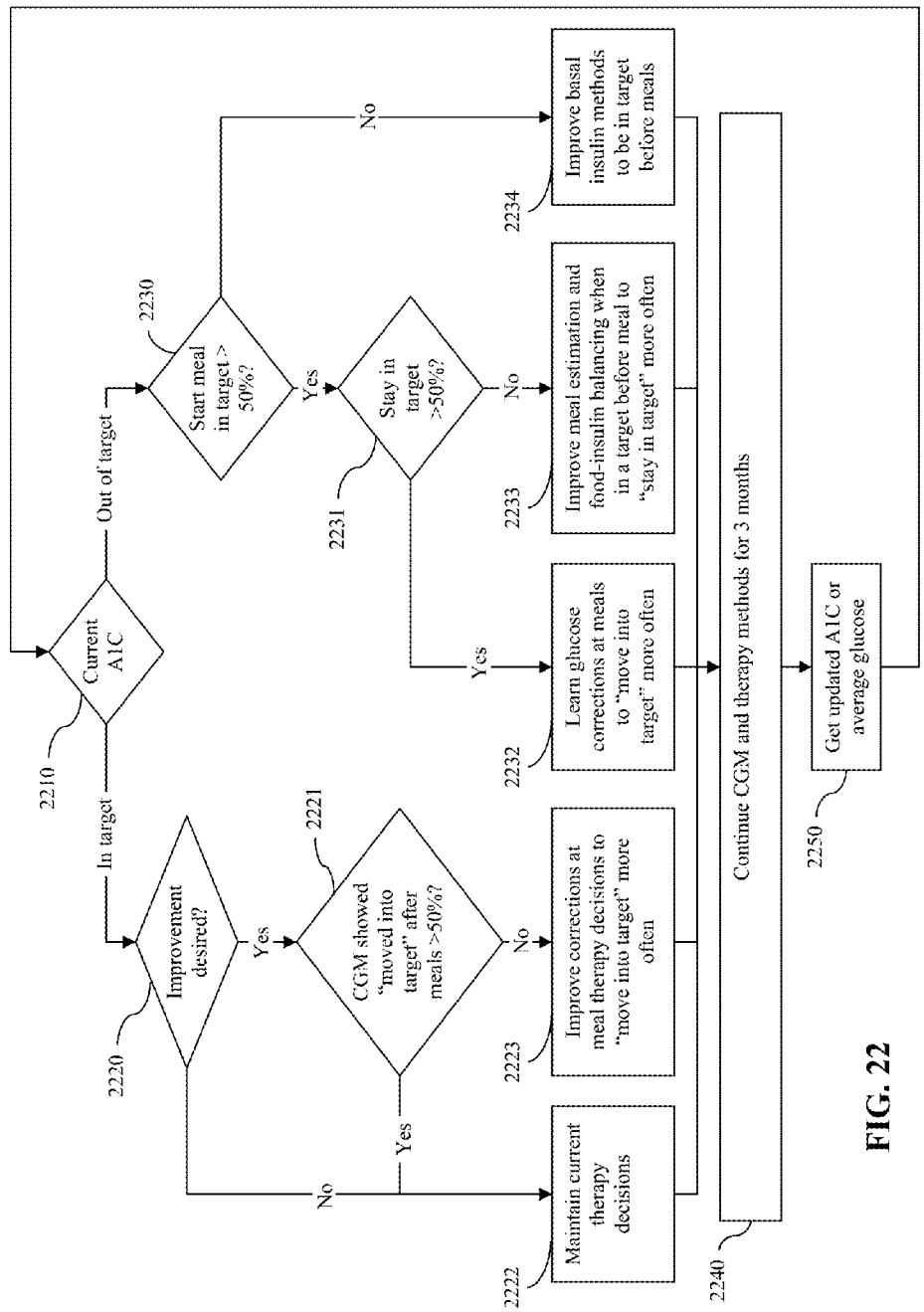
FIG. 22 is a flowchart illustrating a therapy guidance routine based in part on the HbA1C level in one aspect.

FIG. 22 is a flowchart illustrating a therapy guidance routine based in part on the HbA1C level in one aspect. It can be seen from FIG. 22, that the HbA1C level (2210), whether it is in target or out of target is a significant factor in determining or guiding the therapy guidance routine, to determine or prompt the patient to decide whether improvement in HbA1C level (within target range) is desired (2220), and/or to determine whether the start meal in target range that is greater than approximately 50% (2230) as illustrated in the figure. Therapy guidance may also be determined based on such factors as if the HbA1C level moved into the target range (2221) or stayed in the target range (2231).

In aspects of the present disclosure, nonlimiting recommendations based on the routine set forth above (2222, 2223, 2232, 2233, 2234) include, for example, (1) improve understanding and enable improvement of estimates of meal amount and nutrient content, (2) improve understanding and enable adjustment of insulin dose needs, (3) improve understanding and enable adjustment of insulin-to-carbohydrate ratio, (4) improve understanding and enable adjustment of insulin sensitivity ratio, (5) improve understanding of effect of meal choices on glucose control, (6) improve understanding of effect of exercise choices on glucose control, (7) improve understanding of effect of states of health (sickness, menses, stress, other medications) on glucose control, (8) identify patients in need of additional training in different aspects of therapy-decision making, (9) balancing food and insulin, (10) correcting glucose level with insulin, and/or (11) balancing food intake and correcting glucose level with insulin.

Therapy guidelines are followed for a predetermined time period, such as 3 months (2240), before a new HbA1C level is measured (2250). Based on the new measured HbA1C level, therapy management and guidance may be altered accordingly.

In this manner, in one aspect, summary and assessment of glucose control around meal events may be determined that can be effectively understood and acted upon by analyte monitoring system users and their health care providers.

A method in one embodiment, may comprise receiving mean glucose value information of a patient based on a predetermined time period, receiving a current HbA1C level of the patient, determining whether the current HbA1C level of the patient received is within a predefined target range, and if it is determined that the current HbA1C level is not within the predefined target range, determining one or more corrective action for output to the patient, and if it is determined that the current HbA1C level is within the predetermined target range, analyzing the glucose directional change information around one or more meal events, and determining a modification to a current therapy profile.

An apparatus in one embodiment may comprise, a communication interface, one or more processors operatively coupled to the communication interface, and a memory for storing instructions which, when executed by the one or more processors, causes the one or more processors to receive mean glucose value information of a patient based on a predetermined time period, receive a current HbA1C level of the patient, determine whether the current HbA1C level of the patient received is within a predefined target range, if it is determined that the current HbA1C level is not within the predefined target range, determine one or more corrective action for output to the patient, and if it is determined that the current HbA1C level is within the predetermined target range, to analyze the glucose directional change information around one or more meal events, and determining a modification to a current therapy profile.

In one embodiment, a method may include receiving mean glucose value information of a patient based on a predetermined time period, receiving an HbA1C level of the patient, determining a correlation between the received mean glucose value information and the HbA1C level, and determining a target HbA1C level based on the determined correlation.

In one aspect, receiving mean glucose value information may include receiving monitored glucose level information over the predetermined time period, and applying a weighting function to the received monitored glucose level information.

The weighting function may be based on a time of day information associated with the received monitored glucose level information.

The weighting function may be based on a time period associated with the received monitored glucose level information.

In another aspect, determining the target HbA1C level may include receiving one or more patient specific parameters, and applying the received one or more patient specific parameters to the determined correlation between the received mean glucose value information and the received HbA1C level.

The one or more patient specific parameters may include an age of the patient, a history of hypoglycemia, an activity level of the patient, a medication intake information of the patient, or a risk associated with high or low blood glucose levels of the patient.

The determined correlation between the received mean glucose value information and the received HbA1C level may include a rate of glycation of the patient.

The predetermined time period may include one of approximately 30 days, approximately 45 days, or approximately 90 days.

Furthermore, the method may include outputting the determined target HbA1C level.

Furthermore, the method may include storing one or more of the mean glucose value information, the received HbA1C level, the determined correlation between the received mean glucose value information and the HbA1C level, and the determined target HbA1C level.

In another embodiment, an apparatus may include a communication interface, one or more processors operatively coupled to the communication interface, and a memory for storing instructions which, when executed by the one or more processors, may cause the one or more processors to receive mean glucose value information of a patient based on a predetermined time period, receive a HbA1C level of the patient, determine a correlation between the received mean glucose value information and the HbA1C level, and to determine a target HbA1C level based on the determined correlation.

In one aspect, the memory for storing instructions which, when executed by the one or more processors, may cause the one or more processors to receive monitored glucose level information over the predetermined time period, and to apply a weighting function to the received monitored glucose level information.

The weighting function may be based on a time of day information associated with the received monitored glucose level information.

The weighting function may be based on a time period associated with the received monitored glucose level information.

In another aspect, the memory for storing instructions which, when executed by the one or more processors, may cause the one or more processors to receive one or more patient specific parameters, and to apply the received one or more patient specific parameters to the determined correlation between the received mean glucose value information and the received HbA1C level.

The one or more patient specific parameters may include an age of the patient, a history of hypoglycemia, an activity level of the patient, a medication intake information of the patient, or a risk associated with high or low blood glucose levels of the patient.

The determined correlation between the received mean glucose value information and the received HbA1C level may include a rate of glycation of the patient.

The predetermined time period may include one of approximately 30 days, approximately 45 days, or approximately 90 days.

Furthermore, the apparatus may include an output unit operatively coupled to the one or more processors for outputting the determined target HbA1C level.

In another aspect, the memory for storing instructions which, when executed by the one or more processors, may cause the one or more processors to store one or more of the mean glucose value information, the received HbA1C level, the determined correlation between the received mean glucose value information and the HbA1C level, and the determined target HbA1C level.

The various processes described above including the processes performed by the processor 204 (FIG. 2) in the software application execution environment in the analyte monitoring system (FIG. 1) as well as any other suitable or similar processing units embodied in the processing & storage unit 307 (FIG. 3) of the primary/secondary receiver unit 104/106, and/or the data processing terminal/infusion section 105, including the processes and routines described hereinabove, may be embodied as computer programs developed using an object oriented language that allows the modeling of complex systems with modular objects to create abstractions that are representative of real world, physical objects and their interrelationships. The software required to carry out the inventive process, which may be stored in a memory or storage unit (or similar storage devices) in the one or more components of the system 100 and executed by the processor, may be developed by a person of ordinary skill in the art and may include one or more computer program products.

What is claimed is:

1. A method implemented using one or more processors, comprising:
    determining, with one or more processors, a correlation between a mean glucose value information and an HbA1C level associated with a subject;
    determining, with the one or more processors, a rate of glycation of the subject based at least in part on the determined correlation between the mean glucose value information and the HbA1C level;
    applying, with the one or more processors, one or more subject specific parameters to the determined correlation between the mean glucose value information and the HbA1C level;
    determining, with the one or more processors, a target HbA1C level based on determining the rate of glycation of the subject and applying the one or more subject specific parameters to the determined correlation; and
    controlling, with the one or more processors, administration of therapy based on the determined target HbA1C level;
        wherein the one or more subject specific parameters includes an age of the subject, an activity level of the subject, a medication intake information of the subject, or a living condition of the subject.

2. The method of claim 1, wherein the mean glucose value information includes applying a weighting function to monitored glucose level information over a predetermined time period.

3. The method of claim 2, wherein the weighting function is based on a time of day information associated with the monitored glucose level information.

4. The method of claim 2, wherein the weighting function is based on a time period associated with the monitored glucose level information.

5. The method of claim 2, wherein the predetermined time period includes one of approximately 30 days, approximately 45 days, or approximately 90 days.

6. The method of claim 1, further including outputting the determined target HbA1C level.

7. The method of claim 1, further including storing one or more of the mean glucose value information, the HbA1C level, the determined correlation between the mean glucose value information and the HbA1C level, and the target HbA1C level.

8. The method of claim 1, wherein the rate of glycation is a ratio of the mean glucose value information and the HbA1C level.

9. The method of claim 1, wherein the mean glucose value information is obtained using a glucose sensor that comprises a plurality of electrodes including a working electrode.

10. The method of claim 9, wherein the working electrode comprises a glucose-responsive enzyme and a mediator, wherein at least one of the glucose-responsive enzyme and the mediator is chemically bonded to a polymer disposed on the working electrode, and wherein at least one of the glucose-responsive enzyme and the mediator is crosslinked with the polymer.

11. An apparatus, comprising:
one or more processors; and
a memory for storing instructions which, when executed by the one or more processors, cause the one or more processors to determine a correlation between a mean glucose value information and an HbA1C level associated with a subject, to determine a rate of glycation of the subject based at least in part on the determined correlation between the received mean glucose value information and the HbA1C level, to apply one or more subject specific parameters to the determined correlation between the mean glucose value information and the HbA1C level, to determine a target HbA1C level based on determining the rate of glycation of the subject and applying the one or more subject specific parameters to the determined correlation, and to control administration of therapy based on the determined target HbA1C level, wherein the one or more subject specific parameters includes an age of the subject, an activity level of the subject, a medication intake information of the subject, or a living condition of the subject.

12. The apparatus of claim 11, wherein the mean glucose value information includes applying a weighting function to monitored glucose level information over a predetermined time period.

13. The apparatus of claim 12, wherein the weighting function is based on a time of day information associated with the monitored glucose level information.

14. The apparatus of claim 12, wherein the weighting function is based on a time period associated with the monitored glucose level information.

15. The apparatus of claim 12, wherein the predetermined time period includes one of approximately 30 days, approximately 45 days, or approximately 90 days.

16. The apparatus of claim 11, further including an output unit operatively coupled to the one or more processors and configured to output the determined target HbA1C level.

17. The apparatus of claim 11, wherein the memory for storing instructions which, when executed by the one or more processors, further cause the one or more processors to store one or more of the mean glucose value information, the HbA1C level, the determined correlation between the mean glucose value information and the HbA1C level, and the target HbA1C level.

18. The apparatus of claim 11, wherein the rate of glycation is a ratio of the mean glucose value information and the HbA1C level.

19. The apparatus of claim 11, wherein the mean glucose value information is obtained using a glucose sensor that comprises a plurality of electrodes including a working electrode.

20. The apparatus of claim 19, wherein the working electrode comprises a glucose-responsive enzyme and a mediator, wherein at least one of the glucose-responsive enzyme and the mediator is chemically bonded to a polymer disposed on the working electrode, and wherein at least one of the glucose-responsive enzyme and the mediator is crosslinked with the polymer.

* * * * *